US009265828B2

(12) United States Patent
Bennett et al.

(10) Patent No.: US 9,265,828 B2
(45) Date of Patent: Feb. 23, 2016

(54) HYDROGEL IMPLANTS WITH VARYING DEGREES OF CROSSLINKING

(71) Applicant: Covidien LP, Mansfield, MA (US)

(72) Inventors: Steven Bennett, Cheshire, CT (US); Nathaniel Mast, Hamden, CT (US); Kevin Lavigne, Hamden, CT (US); Walter Skalla, Old Lyme, CT (US); Timothy Sargeant, Guilford, CT (US); Joshua Stopek, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 9 days.

(21) Appl. No.: 14/272,720

(22) Filed: May 8, 2014

(65) Prior Publication Data

US 2014/0242024 A1   Aug. 28, 2014

Related U.S. Application Data

(60) Division of application No. 13/222,812, filed on Aug. 31, 2011, now Pat. No. 8,754,564, which is a continuation-in-part of application No. 13/115,079, filed on May 24, 2011, now Pat. No. 8,591,950.

(60) Provisional application No. 61/348,896, filed on May 27, 2010.

(51) Int. Cl.
| | | |
|---|---|---|
| A61K 31/14 | (2006.01) | |
| A61K 41/00 | (2006.01) | |
| A61L 27/52 | (2006.01) | |
| A61L 27/54 | (2006.01) | |
| A61L 29/14 | (2006.01) | |
| A61L 29/16 | (2006.01) | |
| A61L 31/14 | (2006.01) | |
| A61L 31/16 | (2006.01) | |
| A61K 9/00 | (2006.01) | |
| A61K 9/06 | (2006.01) | |
| A61K 47/34 | (2006.01) | |
| A61K 31/00 | (2006.01) | |
| A61L 24/00 | (2006.01) | |
| A61L 26/00 | (2006.01) | |
| C08J 3/075 | (2006.01) | |
| C08J 3/24 | (2006.01) | |

(52) U.S. Cl.
CPC ............ *A61K 41/00* (2013.01); *A61K 9/0024* (2013.01); *A61K 9/06* (2013.01); *A61K 31/00* (2013.01); *A61K 47/34* (2013.01); *A61L 24/0015* (2013.01); *A61L 24/0031* (2013.01); *A61L 26/008* (2013.01); *A61L 26/0066* (2013.01); *A61L 27/52* (2013.01); *A61L 27/54* (2013.01); *A61L 29/145* (2013.01); *A61L 29/16* (2013.01); *A61L 31/145* (2013.01); *A61L 31/16* (2013.01); *C08J 3/075* (2013.01); *C08J 3/246* (2013.01); *A61L 2300/622* (2013.01); *A61L 2300/626* (2013.01); *C08J 2371/02* (2013.01)

(58) Field of Classification Search
USPC .......................................... 606/108; 424/486
See application file for complete search history.

(56) References Cited

U.S. PATENT DOCUMENTS

| | | | |
|---|---|---|---|
| 4,359,049 A | 11/1982 | Redl et al. | |
| 4,631,055 A | 12/1986 | Redl et al. | |
| 4,735,616 A | 4/1988 | Eibl et al. | |
| 4,874,368 A | 10/1989 | Miller et al. | |
| 4,902,281 A | 2/1990 | Avoy | |
| 4,932,942 A | 6/1990 | Maslanka | |
| 4,978,336 A | 12/1990 | Capozzi et al. | |
| 5,116,315 A | 5/1992 | Capozzi et al. | |
| 5,162,430 A | 11/1992 | Rhee et al. | |
| 5,306,500 A | 4/1994 | Rhee et al. | |
| 5,324,775 A | 6/1994 | Rhee et al. | |
| 5,410,016 A | 4/1995 | Hubbell et al. | |
| 5,514,379 A | 5/1996 | Weissleder et al. | |
| 5,543,441 A | 8/1996 | Rhee et al. | |
| 5,550,187 A | 8/1996 | Rhee et al. | |
| 5,752,974 A | 5/1998 | Rhee et al. | |
| 5,874,500 A | 2/1999 | Rhee et al. | |
| 6,152,943 A | 11/2000 | Sawhney | |
| 6,165,201 A | 12/2000 | Sawhney et al. | |
| 6,179,862 B1 | 1/2001 | Sawhney | |
| 6,306,144 B1 * | 10/2001 | Sydney et al. | ................ 606/108 |
| 6,514,534 B1 | 2/2003 | Sawhney | |
| 6,540,789 B1 | 4/2003 | Silverman et al. | |
| 6,566,406 B1 | 5/2003 | Pathak et al. | |
| 6,605,294 B2 | 8/2003 | Sawhney | |
| 6,656,200 B2 | 12/2003 | Li et al. | |
| 6,673,093 B1 | 1/2004 | Sawhney | |
| 6,703,047 B2 | 3/2004 | Sawhney et al. | |

(Continued)

FOREIGN PATENT DOCUMENTS

| | | |
|---|---|---|
| EP | 2 143 737 A1 | 1/2010 |
| EP | 2 196 193 A1 | 6/2010 |
| EP | 2 233 160 A2 | 9/2010 |
| EP | 2 233 161 A2 | 9/2010 |

OTHER PUBLICATIONS

Australian Examination Report dated Dec. 19, 2014 from Appl. No. AU 2011202515.
Examiner's Report issued Mar. 5, 2015 from Australian Appl. No. 2011202507.
European Search Report for EP 11 25 0565.6-2112 date of completion is Dec. 13, 2011 (5 pages).
European Search Report from Application No. EP 10251719.0 mailed May 24, 2013.

*Primary Examiner* — Walter Webb

(57) ABSTRACT

The present disclosure relates to a hydrogel composition and methods of using the same. The hydrogel composition may include precursors that react with each other upon contact as well as precursors that react upon contact with an initiator. In embodiments, the resulting hydrogels may have varying levels of crosslinking with both denser and less dense regions.

9 Claims, 15 Drawing Sheets

(56) References Cited

U.S. PATENT DOCUMENTS

| | | |
|---|---|---|
| 6,818,018 B1 | 11/2004 | Sawhney |
| 7,009,034 B2 | 3/2006 | Pathak et al. |
| 7,347,850 B2 | 3/2008 | Sawhney |
| 8,754,564 B2 | 6/2014 | Bennett et al. |
| 2003/0108511 A1 | 6/2003 | Sawhney |
| 2005/0043814 A1 | 2/2005 | Kusanagi et al. |
| 2005/0266086 A1* | 12/2005 | Sawhney ............. 424/486 |
| 2008/0114092 A1 | 5/2008 | Sawhney |
| 2008/0220047 A1 | 9/2008 | Sawhney et al. |
| 2009/0047349 A1 | 2/2009 | Bennett |
| 2009/0280182 A1 | 11/2009 | Beck et al. |

* cited by examiner

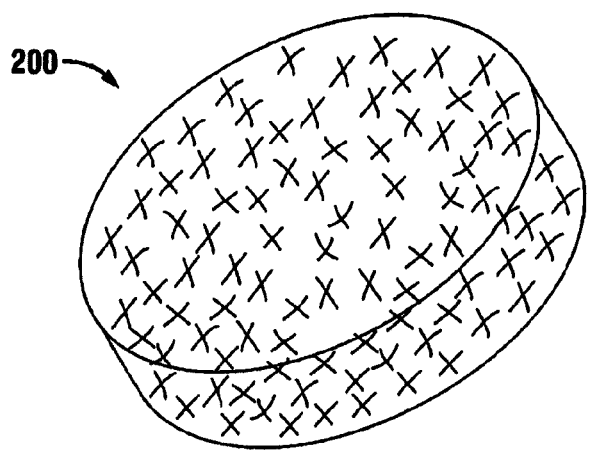
FIG. 2A
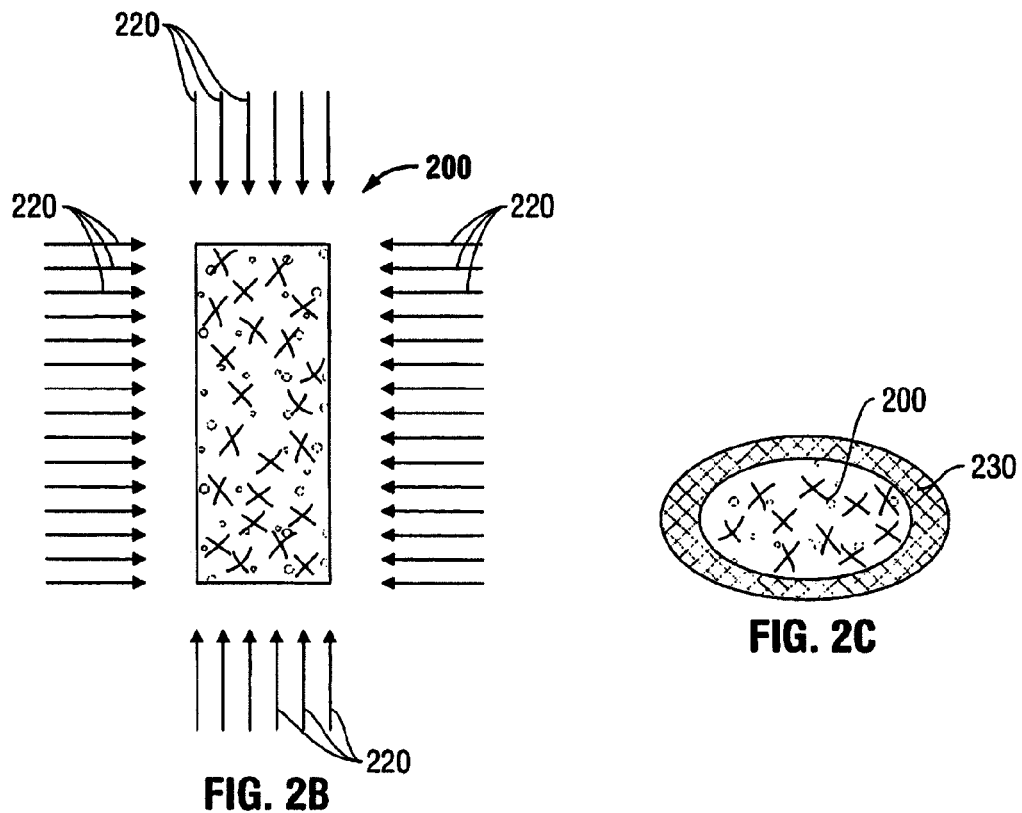
FIG. 2B
FIG. 2C

HYDROGEL IMPLANTS WITH VARYING DEGREES OF CROSSLINKING

CROSS-REFERENCE TO RELATED APPLICATIONS

This application is a divisional of U.S. patent application Ser. No. 13/222,812 filed Aug. 31, 2011, now U.S. Pat. No. 8,754,564, which is a continuation in part of U.S. patent application Ser. No. 13/115,079 filed May 24, 2011, now U.S. Pat. No. 8,591,950, which claims benefit of U.S. Provisional Application No. 61/348,896 filed May 27, 2010, and the disclosures of each of the above-identified applications are hereby incorporated by reference in their entirety.

BACKGROUND

Hydrogels may be used in the body for many different purposes. For example, hydrogels may be used as adhesives or sealants. Hydrogels may also be used in the formation of coatings or implants. Such implants or coatings may also include drugs for local administration.

Hydrogels may be formed from precursor components. These components may be reactive, i.e., the components react with one another upon contact, or they may be caused to react by exposure to external initiators, such as ultraviolet (UV) light, ions, heat, visible light, gamma ray, electron beam, combinations thereof, and the like. Characteristics of the resulting hydrogel may be limited to the characteristics of the particular type of precursor.

It would be advantageous to form a hydrogel that exhibits the properties of both reactive and initiated hydrogel precursors.

SUMMARY

The present disclosure provides hydrogels and methods for making and using same. Devices including these hydrogels are also provided. In embodiments, a method of the present disclosure may include a method of in situ hydrogel formation in a body lumen. Such a method may include introducing a first reactive precursor including electrophilic groups, a second reactive precursor including nucleophilic groups, and an initiated precursor including at least one vinyl group into a body lumen; permitting the first reactive precursor and the second reactive precursor to react to form a first hydrogel capable of adhering to the lumen; and exposing the initiated precursor to an initiator to form a second crosslinked hydrogel, wherein the first hydrogel and the second hydrogel form a composite hydrogel composition.

Kits for producing these compositions are also provided. In embodiments, a kit of the present disclosure may include a first reactive precursor including electrophilic groups, a second reactive precursor including nucleophilic groups, and an initiated precursor including at least one vinyl group; an initiator to initiate crosslinking of the initiated precursor; and a device for introducing the first reactive precursor, the second reactive precursor, the initiated precursor, and the initiator to a body lumen. In some embodiments, the kit may also include an initiator mask to selectively expose the initiated precursor to the initiator.

BRIEF DESCRIPTION OF DRAWINGS

Various embodiments of the present disclosure will be described herein below with reference to the figures, in which:

FIG. 2A is a perspective view of a hydrogel implant in accordance with the present disclosure;

FIG. 2B is a side view of the hydrogel of FIG. 2A depicting exposure to an initiator;

FIG. 2C is a cross-sectional view of the hydrogel of FIG. 2A following exposure to an initiator;

DETAILED DESCRIPTION

Figure 1A:
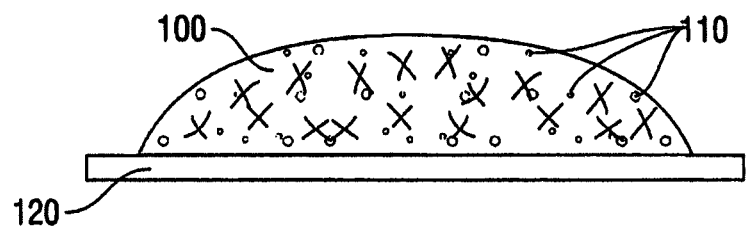
FIG. 1A is a side view of a hydrogel implant in accordance with the present disclosure.

Hydrogels are described herein that may be formed from crosslinking reactive precursors, which do not require the use of an initiator, in combination with precursors that require external initiation, i.e., initiated precursors. The precursor may be, e.g., a monomer or a macromer. As used herein the terms "hydrogel precursor(s)", "first hydrogel precursor", and "second hydrogel precursor" may be used to refer to components that may be combined to form a hydrogel, either with or without the use of an initiator. Thus, these precursors may, in embodiments, include combinations of reactive precursors and initiated precursors. As used herein the terms "reactive precursor(s)", "first reactive hydrogel precursor(s)", and "second reactive hydrogel precursor(s)" include precursors that may crosslink upon exposure to each other to form a hydrogel. As used herein the term "initiated precursor(s)", "first initiated hydrogel precursor(s)" and "second initiated hydrogel precursor(s)" may be used to describe hydrogel precursors that crosslink upon exposure to an external source, sometimes referred to herein as an "initiator". Initiators include, for example, ions, UV light, redox-reaction components, combinations thereof, as well as other initiators within the purview of those skilled in the art.

The hydrogel precursors, whether reactive precursors or initiated precursors, may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose and/or hydroxymethylcellulose; hyaluronic acid; and proteins such as albumin, collagen, casein, and gelatin. In embodiments, combinations of the foregoing polymeric materials may be utilized to form a core. The polyethers, and more particularly poly(oxyalkylenes) or poly(ethylene glycol) or polyethylene glycol ("PEG"), may be utilized in some embodiments.

When the core is small in molecular nature, any of a variety of hydrophilic functionalities may be used to make the hydrogel precursors water soluble. In embodiments, functional groups like hydroxyl, amine, sulfonate and carboxylate, which are water soluble, may be used to make a precursor water soluble. For example, the N-hydroxysuccinimide ("NHS") ester of subaric acid is insoluble in water, but by adding a sulfonate group to the succinimide ring, the NHS ester of subaric acid may be made water soluble, without affecting its ability to be used as a reactive group due to its reactivity towards amine groups.

In embodiments, a hydrogel may be formed from reactive precursors through covalent, ionic, or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ or as a consequence of a prevalent condition in the physiological environment, including temperature, pH, ionic strength, combinations thereof, and the like. Chemical (covalent) crosslinking may be accomplished by any of a number of mechanisms including, but not limited to, free radical polymerization, condensation polymerization, anionic or cationic polymerization, step growth polymerization, electrophile-nucleophile reactions, combinations thereof, and the like.

In embodiments, the reactive precursor portion of the hydrogel may be formed from a single type of reactive precursor or multiple types of reactive precursors. In other embodiments, where the hydrogel is formed from multiple types of reactive precursors, for example two reactive precursors, the reactive precursors may be referred to as a first and second reactive precursor. Where more than one reactive precursor is utilized, in embodiments, at least one of the reactive hydrogel precursors may be a crosslinker, and at least one other reactive hydrogel precursor may be a macromolecule, and may be referred to herein as a "functional polymer".

In some embodiments, reactive precursors may include biocompatible multi-precursor systems that spontaneously crosslink when the precursors are mixed, but wherein the two or more precursors are individually stable for the duration of the deposition process. When the reactive precursors are mixed in an environment that permits reaction (e.g., as relating to pH or solvent), the functional groups react with each other to form covalent bonds. Reactive precursors become crosslinked when at least some of the reactive precursors can react with more than one other precursor. For instance, a precursor with two functional groups of a first type may be reacted with a crosslinking precursor that has at least three functional groups of a second type capable of reacting with the first type of functional groups.

Such reactive components include, for example, first reactive precursors possessing electrophilic groups and second reactive precursors possessing nucleophilic groups. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first reactive precursor may react with a second set of nucleophilic functional groups on a second reactive precursor. In embodiments, such systems include a first reactive precursor including di- or multifunctional alkylene oxide containing moieties, and a second reactive precursor including macromers that are di- or multifunctional amines.

In embodiments the reactive hydrogel precursors may be multifunctional, meaning that they may include two or more electrophilic or nucleophilic functional groups, such that, for example, an electrophilic functional group on the first reactive hydrogel precursor may react with a nucleophilic functional group on the second reactive hydrogel precursor to form a covalent bond. At least one of the first or second reactive hydrogel precursors includes more than two functional groups, so that, as a result of electrophilic-nucleophilic reactions, the precursors combine to form crosslinked polymeric products.

In embodiments, each of the first and second reactive hydrogel precursors include only one category of functional groups, either only nucleophilic groups or only electrophilic functional groups, so long as both nucleophilic and electrophilic reactive precursors are used in the crosslinking reaction. Thus, for example, if the first reactive hydrogel precursor has electrophilic functional groups such as N-hydroxysuccinimides, the second reactive hydrogel precursor may have nucleophilic functional groups such as amines. On the other hand, if the first reactive hydrogel precursor has electrophilic functional groups such as sulfosuccinimides, then the second reactive hydrogel precursor may have nucleophilic functional groups such as amines or thiols.

In embodiments, a multifunctional electrophilic polymer such as a multi-arm PEG functionalized with multiple NHS groups may be used as a first reactive hydrogel precursor and a multifunctional nucleophilic polymer such as trilysine may be used as a second reactive hydrogel precursor. The multi-arm PEG functionalized with multiple NHS groups may, for example, have four, six or eight arms and a molecular weight of from about 5,000 to about 25,000. Other examples of suitable first and second reactive hydrogel precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated by reference herein.

Certain properties of a hydrogel precursor may be useful, including, for example, adhesion to a variety of tissues, desirable setting times to enable a surgeon to accurately and conveniently place the in situ forming hydrogel precursors, high water content for biocompatibility, mechanical strength for use in sealants, and/or toughness to resist destruction after placement. Synthetic materials that are readily sterilized and avoid the dangers of disease transmission that may accompany the use of natural materials may thus be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

The reaction conditions for forming crosslinked polymeric hydrogels from reactive precursors may depend on the nature of the reactive precursor used. In embodiments, reactions are conducted in buffered aqueous solutions at a pH of about 5 to about 12. Buffers include, for example, sodium borate buffer (pH 10) and triethanol amine buffer (pH 7). In some embodiments, organic solvents such as ethanol or isopropanol may be added to improve the reaction speed or to adjust the viscosity of a given formulation.

When the hydrogel precursors are synthetic (for example, when they are based on polyalkylene oxide), it may be desirable to use molar equivalent quantities of the reactants. In some cases, molar excess of a crosslinker may be added to compensate for side reactions such as reactions due to hydrolysis of the functional group.

When choosing the reactive precursors, in embodiments a crosslinker and crosslinkable polymer, at least one of the polymers may have more than two functional groups per molecule and, if it is desired that the resultant hydrogel be biodegradable, at least one degradable region. In embodiments, each reactive polymer precursor may have more than two functional groups, and in embodiments, more than four functional groups.

The crosslinking density of the resultant biocompatible, crosslinked polymer formed from the reactive precursors may be controlled by the overall molecular weight of the precursors, in embodiments a crosslinker and functional polymer, and the number of functional groups available per molecule. A lower molecular weight between crosslinks, such as 600 Da, will give much higher crosslinking density as compared to a higher molecular weight, such as 10,000 Da. Elastic gels may be obtained with higher molecular weight functional polymers with molecular weights of more than 3000 Da.

The crosslinking density may also be controlled by the overall percent solids of the precursors, in embodiments crosslinker and functional polymer, in solutions. Increasing the percent solids increases the number of crosslinkable groups per unit volume and potential crosslinking density. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

In embodiments, a first reactive precursor may be a multi-arm PEG and may be functionalized by ring opening anhydrides containing a vinyl group and end capped with NHS. The second reactive precursor may be a multifunctional amine component. The hydrogel of the disclosure may thus be formed from at least two precursors.

In some embodiments, as noted above, hydrogel precursors may include initiated precursors. Initiated precursors for use in accordance with the present disclosure may have a functional group that is ethylenically unsaturated. Such precursors possessing such ethylenically unsaturated functional groups may have biologically inert and water soluble cores as described above. Such cores may be functionalized by any means within the purview of those skilled in the art.

An ethylenically unsaturated functional group, in embodiments a vinyl group, may be polymerized using an initiator to start the polymerization reaction. Precursors with at least two ethylenically unsaturated functional groups may form crosslinked polymers. Some compositions have certain precursors with only one such functional group and additional crosslinked precursors with a plurality of functional groups for crosslinking the precursors. Ethylenically unsaturated functional groups may be polymerized by various techniques, e.g., free radical, condensation, or addition polymerization. Exemplary initiated precursors that may be used in accordance with the present disclosure include acrylates; anhydrides containing vinyl groups such as, for example, itaconic anhydride, maleic anhydride, citraconic anhydride, combinations thereof, and the like. Other exemplary initiated precursors include, for example, acrylic acid, methacrylic acid, phosphorylcholine containing monomers, furanone functional vinyl monomers, potassium sulfopropyl acrylate, potassium sulfopropyl methacrylate, n-vinyl pyrrolidone, hydroxyethyl methacrylate, vinyl monomers having a high refractive index, siloxane functional vinyl compounds, polyethylene glycol-silicone co-monomers having vinyl groups, tris acrylate, pyrrole, liquid crystalline vinyl monomers, liquid crystalline vinyl polymers, combinations thereof, and the like.

Suitable initiators utilized to polymerize initiated precursors include, but are not limited to, thermal initiators, photo-activatable initiators, oxidation-reduction (redox) systems, free radical initiators, radiation, thermal initiating systems, combinations thereof, and the like. In embodiments, suitable sources of radiation include heat, visible light, ultraviolet (UV) light, gamma ray, electron beam, combinations thereof, and the like. In embodiments, photoinitiators may also be used. Such photoinitiators include, but are not limited to, free radical initiators, redox initiators such as ferrous-bromate, ammonium persulfate/acetic acid, ammonium persulfate-tetramethyl diamine, potassium persulfate/VA 044 (Wako Chemicals Inc., Richmond Va.), and the like. UV light may also be used with dye mediated photooxidation, glutaraldehyde crosslinking, dexamethylene diisocyanate crosslinking, carbodiimide crosslinking, combinations thereof, and the like.

In embodiments, one or more hydrogel precursors having biodegradable linkages present in between functional groups may be included to make the hydrogel biodegradable or absorbable. In some embodiments, these linkages may be, for example, esters, which may be hydrolytically degraded in physiological solution. The use of such linkages is in contrast to protein linkages that may be degraded by proteolytic action. A biodegradable linkage may also form part of a water soluble core of one or more of the hydrogel precursors. Alternatively, or in addition, functional groups of hydrogel precursors may be chosen such that the product of the reaction between them results in a biodegradable linkage. For each approach, biodegradable linkages may be chosen such that the resulting biodegradable, biocompatible, crosslinked polymer degrades or is absorbed in a desired period of time. Generally, biodegradable linkages may be selected that degrade the hydrogel under physiological conditions into non-toxic or low toxicity products.

Biodegradable crosslinkers or small molecules as described above may be reacted with proteins, such as albumin, other serum proteins, and/or serum concentrates, to generate crosslinked polymeric networks. Generally, aqueous solutions of crosslinkers may be mixed with concentrated solutions of proteins to produce a crosslinked hydrogel. The reaction may be accelerated by adding a buffering agent, e.g., a borate buffer or triethanol amine, during the crosslinking step.

The crosslinking reaction leading to gelation may occur, in embodiments, within from about 1 second to about 5 minutes, in embodiments from about 3 seconds to about 1 minute. Persons of ordinary skill in these arts will immediately appreciate that all ranges and values within these explicitly stated ranges are contemplated. In some cases gelation may occur in less than 10 seconds.

Degradation of a crosslinked hydrogel may depend upon the biodegradable segment in the crosslinker as well as any enzymes to which the hydrogel is exposed. In the absence of any degrading enzymes, the crosslinked polymer may degrade solely by hydrolysis of the biodegradable segment. The rate of degradation may depend upon the polymer forming the water soluble core and more specifically on the structure and location of any ester linkages formed. For example, an ester linkage may be formed in a ring opening polymerization. The ring opening polymerization may occur, for example, between a PEG and a cyclic ester or an anhydride including, for example, furan-2,5-dione, 1,4-dioxane-2,5-dione, glutaric anhydride, succinic acid anhydride, maleic anhydride, itaconic anhydride, methyl succinic anhydride, 2,2-dimethyl succinic anhydride, 2 dodecen-1-yl succinic anhydride, cis-1,2,3,6-tetrahydrophthalic anhydride, citraconic anhydride, 2,3-dimethyl maleic anhydride, 1-cyclopentene-1,2-dicarboxylic anhydride, 3,4,5,6-tetrahydrophthalic anhydride, 3 ethyl-3-methyl glutaric anhydride, 3,3-dimethyl glutaric anhydride, 3-methyl glutaric anhydride, combinations thereof, and the like. The resulting polymer may then be functionalized, in embodiments with a succinimide group, and then may be utilized as a reactive precursor to form a hydrogel of the present disclosure (for example, by combining with a crosslinker such as an amine). The monomer combined with PEG for the ring opening polymerization, and thus the resulting degradable ester group, will influence the persistence of the hydrogel in vivo. The percent solids and arm length of monomers used to form this reactive precursor may also influence its degradation rate.

For example, in embodiments, the product may be the ring opening polymerization between PEG and a second component including an anhydride such as glutaric anhydride, itaconic anhydride, methyl succinic anhydride, 2,2-dimethyl succinic anhydride, 2 dodecen-1-yl succinic anhydride, cis-1,2,3,6-tetrahydrophthalic anhydride, citraconic anhydride, 2,3-dimethyl maleic anhydride, 1-cyclopentene-1,2-dicarboxylic anhydride, 3,4,5,6-tetrahydrophthalic anhydride, 3 ethyl-3-methyl glutaric anhydride, 3,3-dimethyl glutaric anhydride, 3-methyl glutaric anhydride, combinations thereof, and the like. The resulting product may form a hydrogel that degrades over a period of from about 6 weeks to about 8 weeks.

In other embodiments, the product of the ring opening polymerization between PEG and succinic acid anhydride may degrade over a period of from about 2 days to about 7 days. In embodiments where PEG and maleic anhydride are used, the product may degrade over a period of about six months. The vinyl group in the ring opened maleic anhydride may be involved in a secondary vinyl polymerization. Thus, in embodiments, the vinyl group of the ring opened maleic anhydride may serve as an initiated precursor.

The hydrophobicity generated by biodegradable blocks such as oligohydroxy acid blocks or the hydrophobicity of PPO blocks in PLURONIC or TETRONIC polymers may be helpful in dissolving small organic drug molecules. Other properties which will be affected by incorporation of biodegradable or hydrophobic blocks include: water absorption; mechanical properties; and thermosensitivity.

Synthetic crosslinked gels degrade due to hydrolysis of the biodegradable region. The degradation of gels containing synthetic peptide sequences may depend on the specific enzyme necessary for degradation of the sequence and its concentration. In some cases, a specific enzyme may be added during the crosslinking reaction to accelerate the degradation process.

The hydrogel precursors may be placed into solution prior to use, with the solution being delivered to tissue. Where two solutions are employed, each solution may contain one or more precursors that may react with one another upon contact. The solutions may be separately stored and mixed when delivered to tissue.

Any solutions utilized as part of an in situ forming material system should not contain harmful or toxic solvents. In embodiments, the precursor(s) may be substantially soluble in a solvent such as water to allow application in a physiologically-compatible solution, such as buffered isotonic saline. Water-soluble coatings may form thin films, but in embodiments may also form three-dimensional gels of controlled thickness. The gel may also be biodegradable, so that it does not have to be retrieved from the body. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Various applications may require different characteristics of the hydrogel. Generally, the hydrogel precursors should be selected on the basis of exhibited biocompatibility and lack of toxicity.

In embodiments, a hydrogel may be formed from at least one reactive precursor (capable of crosslinking, for example, by free radical polymerization), and at least one initiated precursor, or made with three or more precursors, with one or more of the precursors participating in crosslinking to form the in situ forming material.

Prior to hydrogel formation, the initiated precursor, in embodiments a linear PEG acrylate, may be reconstituted in a high pH buffer, for example sodium borate, having a pH from about 7 to about 11, in embodiments from about 8 to about 10. The initiated precursor, in embodiments a multi-arm PEG having electrophilic functional groups, may be reconstituted with a low pH buffer, such as, sodium phosphate, having a pH from about 3 to about 6, in embodiments from about 4 to about 5.

In embodiments, a linear PEG acrylate may be used as the initiated precursor. In embodiments, a hydrogel may thus be formed by contacting a first reactive hydrogel precursor, a second reactive hydrogel precursor, and the initiated precursor. The hydrogel may form upon reaction of the first reactive precursor and the second reactive precursor. The components may also be exposed to an initiator to crosslink the initiated precursor thereby creating a denser hydrogel.

In embodiments, the resulting hydrogel may form an interpenetrating network. In embodiments, an interpenetrating network may be formed from two hydrogel networks, i.e., a hydrogel formed by at least two reactive precursors in combination with an initiated precursor. In other embodiments, the interpenetrating network could be formed from an initiated precursor that also possesses reactive groups. Such a precursor can both react with another reactive precursor and be initiated upon exposure to an initiator.

For example, in embodiments, a first hydrogel may form between a multi-arm PEG and trilysine. A second hydrogel may be formed by exposing an ethylenically unsaturated monomer to an initiator. These two hydrogels may be combined prior to exposure to the initiator. Exposure of these hydrogels, to the initiator results in an interpenetrating network of hydrogels, each of which may have separate properties such as varying degradation rates. Additionally, varying the amount of reactive precursors and initiated precursors may result in different properties of the resulting composition.

In other embodiments, a multi-arm PEG may be functionalized with vinyl groups and reacted with trilysine to form a first hydrogel. By initiating the PEG functionalized with vinyl groups with an initiator, the crosslinking of the hydrogel may be increased due to the crosslinking of the vinyl groups, thereby forming an interpenetrating network. In other embodiments, a multi-arm PEG functionalized with vinyl groups may react to a limited extent with amines, followed by the addition of an initiator to increase crosslinking of the vinyl groups.

Where the reactive precursors from a first hydrogel, the initiated precursor forms a second hydrogel, and the two hydrogels together form an interpenetrating network, in embodiments the first hydrogel formed from the reactive precursors may degrade more quickly than the second hydrogel formed from the initiated precursor, thereby forming spaces permitting healing by means of, for example, tissue in-growth, vascularization, combinations thereof, and the like.

In embodiments, the hydrogel of the present disclosure, having an interpretation network with varying degrees of degradation, may act as a tissue scaffold, thereby providing a means for tissue integration/ingrowth. Tissue scaffolds also are capable of providing cells with growth and development components. Thus, where the hydrogel of the present disclosure is utilized as a tissue scaffold, it may assist in native tissue regrowth by providing the surrounding tissue with needed nutrients and bioactive agents. In some embodiments, as discussed herein, the hydrogel itself may include a natural component, such as collagen, gelatin, hyaluronic acid, combinations thereof, and the like, and thus the natural component may be released or otherwise degrade at the site of implantation as the tissue scaffold degrades.

In other embodiments, a hydrogel composition of the present disclosure may possess two hydrogels, with one dispersed within the other. For example, in embodiments, a composition of the present disclosure may include the first hydrogel formed from reactive precursors, with at least one disperse region within the first hydrogel, the disperse region formed of a second hydrogel formed from an initiated precursor. In other embodiments, a first hydrogel formed of reactive precursors may form at least one disperse region within a second hydrogel formed from an initiated precursor. The disperse region formed by one hydrogel may form one region, e.g., a central region or core, within a second hydrogel, or the disperse region formed by one hydrogel may form many small regions within a second hydrogel.

Varying the concentrations of the reactive and initiated precursors may result in differing properties of the resulting hydrogel. For example, in embodiments, a solution may contain an acrylate having a molecular weight from about 200 g/mole to about 50,000 g/mole, in embodiments from about 500 g/mole to about 35,000 g/mole, at a concentration of from about 5 g/ml to about 40 g/ml, in embodiments about 10 g/ml to about 20 g/ml. The solution may also contain a photoinitiator at a concentration of from about 5 mg/ml to about 100 mg/ml, in embodiments from about 10 mg/ml to about 20 mg/ml. The photoinitiator may be, for example, 4,4'-Bis(diethyl amino)benzophenone, 2,2-dimethoxy-2-phenyl acetophenone, camphorquinone/4-dimethyl amino benzoic acid, eosin, azobisisobutyronitrile (AIBN), dimethoxy benzophenone, combinations thereof, and the like. The acrylate/photoinitiator solution may have a concentration from about 4.25% to about 17%, in embodiments from about 6% to about 14%, in embodiments about 8.5%. In embodiments the acrylate/photoinitiator solution may be combined with a multi-arm PEG may be in a sodium phosphate buffer at a concentration of from about 0.05 g/ml to about 2 g/ml, in embodiments about 0.1 g/ml to about 1 g/ml, in embodiments about 0.26 g/ml. These solutions may react to form a hydrogel of the present disclosure.

Figure 4:
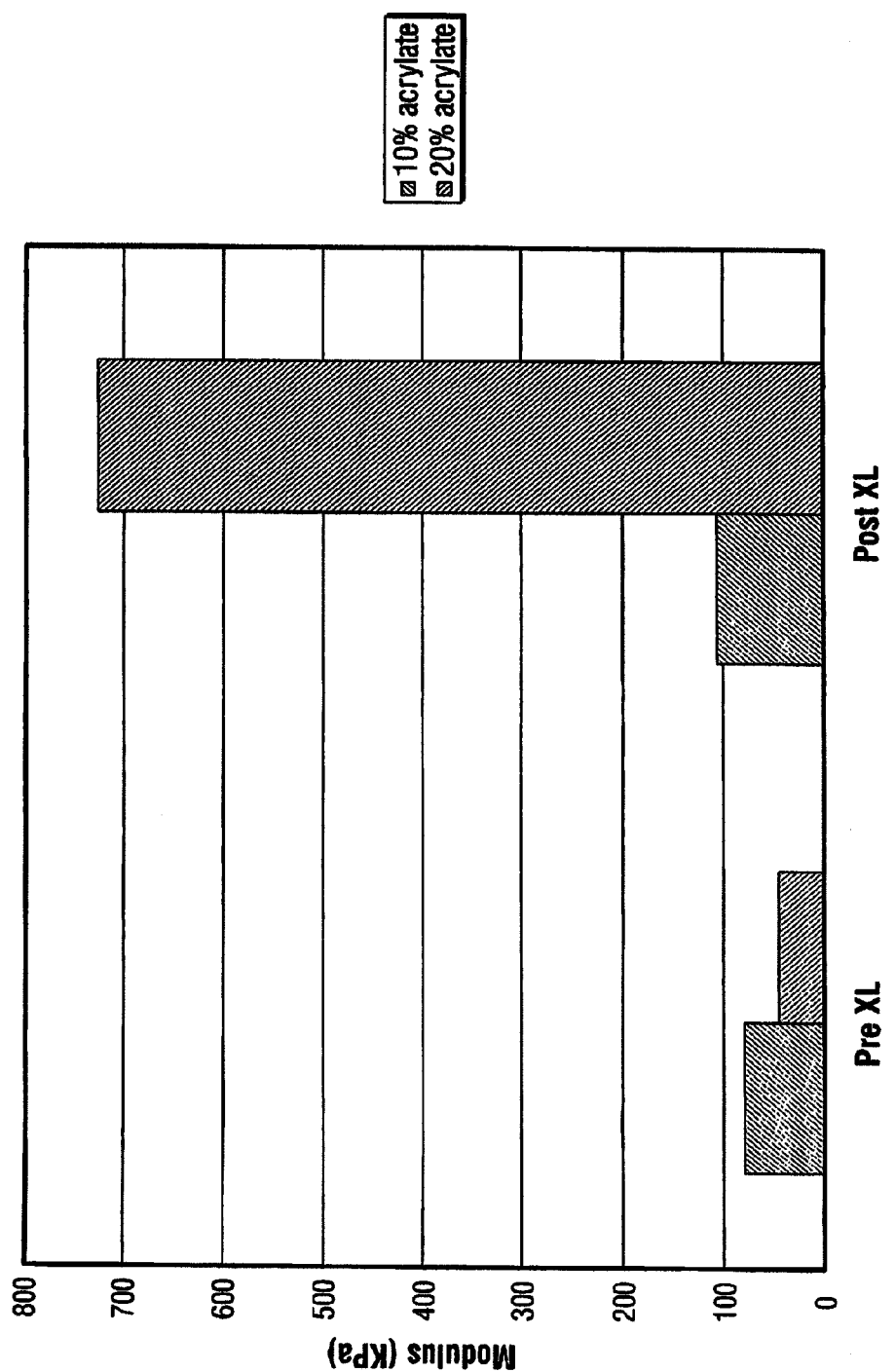
FIG. 4 is a graph depicting the modulus of a hydrogel implant of the present disclosure prior to and following cross-linking of an initiated precursor.

As stated above, addition of the initiated precursor to the reactive precursors and subsequent exposure to an initiator may alter properties of the resulting hydrogel. Additionally, the ratio of initiated precursor to reactive precursors may influence mechanical properties. As depicted graphically in FIG. 4 and listed in Table 1 below, the percentage of initiated precursor present in the mixture of reactive and initiated precursors greatly impacts the strength of the hydrogel following cross-linking of the reactive hydrogels.

TABLE 1

| | Hydrogel | | | |
|---|---|---|---|---|
| | 10% initiated (uncrosslinked): 90% reactive | 20% initiated (uncrosslinked): 80% reactive | 10% initiated (crosslinked): 90% reactive | 20% initiated (crosslinked): 80% reactive |
| Modulus (KPa) | ~80 Kpa | ~40 KPa | ~100 KPa | ~720 KPa |

Thus, in accordance with the present disclosure, a hydrogel may be formed by two different mechanisms: the reaction of the reactive precursors; and the initiation of the initiated precursors. The resulting hydrogel may, in turn, thus be made of two different hydrogels. For example, a first hydrogel may be formed from the reactive precursors, while a second hydrogel may be formed from the initiated precursors.

The first hydrogel may include the first reactive precursor in an amount from about 10% to about 30%, in embodiments from about 15% to about 25%, and the second reactive precursor in an amount from about 70% to about 90%, in embodiments from about 75% to about 85%. In other embodiments, the first hydrogel may include the first reactive precursor in an amount from about 70% to about 90%, in embodiments from about 75% to about 85%, and the second reactive precursor in an amount from about 10% to about 30%, in embodiments from about 15% to about 25%.

The modulus of the materials utilized to form a composition of the present disclosure may depend upon the end use of the composition. For example, a composition applied to tissue for use as a tissue scaffold may have a much lower modulus than a composition intended for use to attach a medical device to tissue.

In embodiments, the first hydrogel formed from the reactive precursors may have a modulus from about 5 kilopascal (kPa) to about 90 kPa, in embodiments from about 10 kPa to about 50 kPa, and the second hydrogel formed from the initiated precursor may have a modulus from about 50 kPa to about 5,000 kPa, in embodiments from about 100 kPa to about 4,000 kPa.

Depending on the degradation rates of the resulting hydrogels, the portion of the hydrogel formed by the reactive precursors may degrade more quickly than the portion of the hydrogel formed by the initiated precursor, thereby forming spaces in the hydrogel which may permit tissue in-growth, visualization, and the like. In embodiments, the first hydrogel formed from reactive precursors may degrade over a period of time from about 1 week to about 12 weeks, in embodiments from about 4 weeks to about 10 weeks, while the second hydrogel formed from initiated precursors may degrade over a period of at least about 2 weeks, in embodiments it may not degrade, i.e., it remains permanently in the body. In some embodiments the second hydrogel may degrade over a period of at least about 6 months. In some embodiments, the second hydrogel may degrade over a period from about 6 weeks to about 6 months.

Where the second hydrogel forms a barrier layer over the first hydrogel, the first hydrogel may have a modulus from about 5 kPa to about 60 kPa, in embodiments from about 10 kPa to about 50 kPa, and the second hydrogel forming the barrier layer may have a modulus from about 100 kPa to about 1,000 kPa, in embodiments from about 200 kPa to about 900 kPa. The first hydrogel may thus degrade over a period from about 1 day to about 7 days, in embodiments from about 2 days to about 6 days, and the barrier layer may degrade over a period of at least about 6 months, in embodiments from about 6 months to about 12 months.

Where the hydrogels form an interpenetrating network, the first hydrogel may have a modulus from about 5 kPa to about 20 kPa, in embodiments from about 8 kPa to about 17 kPa, and the second hydrogel may have a modulus from about 50 kPa to about 500 kPa, in embodiments from about 75 kPa to about 400 kPa.

Where the hydrogel is used to form an attachment device for attaching a medical device to tissue, the first precursor may have a modulus from about 10 kPa to about 50 kPa, in embodiments from about 15 kPa to about 45 kPa, and the second hydrogel may have a modulus from about 60 kPa to about 200 kPa, in embodiments from about 75 kPa to about 175 kPa. The initiated precursor forming the second hydrogel may be present in an amount from about 40% to about 90% by weight of the attachment device, in embodiments from about 50% to about 75% by weight of the attachment devices. The first hydrogel may degrade over a period from about 1 day to about 7 days, in embodiments from about 2 days to about 6 days, and the second hydrogel may degrade over a period of at least about 6 months, in embodiments from about 6 months to about 12 months.

Where the composition of the present disclosure is used to deliver a bioactive agent, the first hydrogel may have a modulus from about 5 kPa to about 50 kPa, in embodiments from about 10 kPa to about 40 kPa, and the second hydrogel may have a modulus from about 10 kPa to about 100 kPa, in embodiments from about 20 kPa to about 80 kPa.

In embodiments, one reactive precursor and one initiated precursor may be placed in a first solution, and a second reactive precursor with an optional initiated precursor may be placed in a second solution. Upon the mixture of these solutions, the reactive precursors may crosslink to form a base hydrogel, while the initiated precursors may not crosslink until exposed to an initiator. In other embodiments, one reactive precursor and one or more initiated precursor(s) may be placed in a first solution, and a second reactive precursor may be placed in a second solution.

The density of a hydrogel resulting from a combination of reactive precursors and initiated precursors may be further controlled based on the initiator used to form the hydrogel. For example, a multi-arm PEG capped with NHS first reactive hydrogel precursor, a multifunctional amine second reactive hydrogel precursor, and a linear PEG acrylate initiated precursor, may result in a hydrogel containing unreacted acrylate groups. Upon exposure to an initiator, in embodiments UV light, the acrylate groups may react with themselves as well as the terminal ends of the PEG arms. By controlling exposure to the initiator, the amount of acrylate crosslinking may thus be used to further adjust the density of the hydrogel.

Adjustment of the density of the hydrogel may affect the permeability of the resulting hydrogel, e.g., a denser hydrogel may be less permeable. In embodiments, the initiated precursor(s) may be densely crosslinked, thereby forming a less permeable barrier layer within or on the exterior of the hydrogel formed from the reactive precursors, thus forming a composite hydrogel composition.

In accordance with the present disclosure, the polymer formed from an initiated precursor may account for from about 5 percent by weight to about 30 percent by weight of the resulting composite hydrogel, in embodiments from about 10 percent by weight to about 20 percent by weight of the resulting hydrogel, with the polymer formed from the reactive precursors accounting for from about 5 percent by weight to about 60 percent by weight of the resulting hydrogel, in embodiments from about 15 percent by weight to about 40 percent by weight of the resulting hydrogel. The remainder of the resulting hydrogel will be made up of fluid/water.

Formation of a hydrogel of the present disclosure may take place in situ. In other embodiments, the hydrogel formation may take place ex vivo, that is, prior to placement in situ. The combination of reactive precursors with initiated precursors may allow for the formation of hydrogels that exhibit properties of both types of crosslinked precursors. In some embodiments, the hydrogel may be molded into a desired shape within a tissue defect prior to exposing a surface of the hydrogel to an initiator.

In situ formation, in general, may be accomplished by having a hydrogel precursor that may be activated at the time of application to tissue to form a crosslinked hydrogel. Activation may be made before, during, or after application of the precursor to tissue. Activation includes, for instance, triggering a polymerization process, initiating a free radical polymerization, or mixing precursors with functional groups that react with each other. Thus, in situ polymerization includes activation of chemical moieties to form covalent bonds and to create an insoluble material, e.g., a hydrogel, at a location where the material is to be placed on, within, or both on and within, a patient. In situ polymerizable polymers may be prepared from hydrogel precursors that may be reacted such that they form a polymer within the patient. As noted above, in embodiments, a hydrogel may be formed from both reactive precursors and initiated precursors.

As stated above, the hydrogel precursors may be placed into solution prior to use, with the solution being delivered to the patient. In embodiments, the precursors may be substantially soluble in water to allow application in a physiologically-compatible solution, such as buffered isotonic saline. One may use a dual syringe or similar device to apply the precursor solutions, such as those described in U.S. Pat. Nos. 4,874,368; 4,631,055; 4,735,616; 4,359,049; 4,978,336; 5,116,315; 4,902,281; 4,932,942; 6,179,862; 6,673,093; 6,152,943; and 7,347,850.

Generally, two or more hydrogel precursors may be applied via a sprayer to the tissue to form a coating in situ. For example, two reactive precursor solutions, at least one of which containing an initiated precursor, may be placed in separate chambers of the sprayer. When the sprayer is activated, the emergent spray contacts tissue, resulting in mixing and crosslinking of the two reactive precursors to form a coating (for example a hydrogel) on the tissue surface.

In embodiments, the sprayer includes separate spray nozzles for each of two or more reactive precursor solutions, with each nozzle surrounded by a separate or common gas flow outlet. The reactive precursor solutions are stored in separate compartments, e.g., a multi-cylinder syringe, and transferred under pressure to the spray nozzles. In the presence of gas flow through the gas flow outlets, the crosslinkable solutions are atomized and mixed in the gas flow to form a spray, which may be used to coat tissue. In certain embodiments, a $CO_2$ gas cartridge may be reversibly or permanently mounted on the device to facilitate delivery of the precursors.

Certain embodiments include combining a suction-irrigation apparatus with a hydrogel precursor delivery device. An advantage of such a combination is that the tissue may be cleansed of clotted blood and adhesioniogenic materials and the combination may allow for placement of a hydrogel using a single device.

The hydrogel of the present disclosure may also be used to form, for example, components such as adhesives, hemostats, sealants, implants, protective barriers, drug delivery devices, combinations thereof, and the like. Implants which may be formed include, for example, matrices, artificial blood vessels, heart valves, artificial organs, bone prostheses, implantable lenticules, vascular grafts, stents, sutures, staples, clips, meshes, slings, screws, pins, cables, cartilage implants, spinal implants, and combinations thereof. The implant may also be used to augment of soft or hard tissue within the body of a mammal. Examples of soft tissue augmentation applications include: sphincter (e.g., urinary, anal, esophageal) augmentation; use as artificial skin; the treatment of rhytids; and/or the treatment of scars. Examples of hard tissue augmentation include the repair and/or replacement of bone and/or cartilaginous tissue. Other tissue defects which may be treated with a hydrogel and/or implant of the present disclosure include, for example, sphincters, including lower esophageal sphincter bulking to treat gastroesophageal reflux disease (GERD); periurethral bulking to treat urinary incontinence; creating cushions between tissue layers to assist in tissue dissections and/or resections, for example in polypectomy procedures; preventing adhesions; plastic surgery as a dermal filler; treatment of defects in lips, breasts, and other body tissues; combinations thereof, and the like.

In embodiments, the hydrogel may be used to form a semi-flexible vertebral disc having a rigid or dense exterior formed by the hydrogel produced by the initiated precursor and a less dense, more flexible, interior formed by the hydrogel produced by the reactive precursors. In embodiments, a template may be used that is shaped to resemble the vertebral disc needing replacement. The template may be filled with the hydrogel precursors to form the hydrogel. The hydrogel may then be exposed to an initiator so as to induce crosslinking of the initiated precursor on the surface, thereby forming a dense outer or barrier layer encompassing the hydrogel interior.

For formation of a vertebral disc implant, the implant may be formed during surgery, or prior to surgery. For example, the appropriate implant size may be determined during surgery by first using a caliper or similar device to measure the length and dimensions of the defect to be repaired. The surgical staff may then utilize a template as described above to form an implant of the desired size by introducing the reactive precursors and initiated precursor into the template and allowing the reactive precursors to form the first hydrogel. The composition may then be subjected to the initiator, thereby forming the dense outer or barrier layer encompassing the first hydrogel interior, thereby producing the vertebral disc implant.

Alternatively, using radiographic techniques, including X-ray, MRI, and the like, the appropriate implant size may be determined pre-operatively, with the vertebral disc implant formed as described above prior to surgery.

In other embodiments, the reactive precursors may be applied to a defect in tissue, thereby forming a first hydrogel therein, with the initiated precursor forming a second hydrogel, which functions as a barrier layer, on at least a portion of a surface of the first hydrogel covering the defect in tissue.

The selection of materials for forming the hydrogels may be tailored depending upon the end use of the hydrogel composition of the present disclosure. For example, polyethylene glycol-based polymers may be desirable where protein adhesion is to be prevented; hyaluronic acid-based polymers may be desirable where enhanced sliding, gliding, and/or lubricity is desired; collagen-based polymers may be desirable to provide adhesion sites for cellular attachment; synthetic polymers may be desirable for long-term and/or permanent implants; and the like.

In embodiments, reactive hydrogel precursors may form a hydrogel containing a bioactive agent. An initiated precursor may be added to the precursors prior to or following reaction. The initiated precursor may then be initiated forming a barrier layer. The barrier layer may inhibit diffusion of the bioactive agent from the hydrogel formed by the reactive precursors in the direction of the barrier, thereby forcing unidirectional administration of the bioactive agent, i.e., in a direction opposite the barrier layer.

In embodiments, reactive and initiated hydrogel precursors may also be combined in a layer on the bottom of a mold. The base layer may then be exposed to an initiator to further cross-link the bottom layer. A second layer including the precursors may then be placed on the bottom layer and a screen may be used to limit the exposure of the second layer to the initiator. Thus, the un-screened portion may further crosslink, while the screened portion does not crosslink, thereby providing varying degrees of cross-linking in the layer. Additional layers may be added using the same or different screens. Each layer may contain a bioactive agent which may be the same or different. The varied amount of crosslinking may provide alternate rates of degradation, thereby providing varying release rates of the bioactive agent. The initiator may be contacted with the hydrogel before or after contact with the medical device. Medical devices which may be attached to tissue with the hydrogel include sutures, staples, tacks, clips, rivets, combinations thereof, and the like.

In other embodiments, a mixture of reactive and initiated hydrogel precursors may be sprayed or applied to an implant such as a mesh. The mesh may be a filamentous substrate including an initiator for the initiated hydrogel. The reactive hydrogel may form a coating over the mesh. The coating may degrade over several days, thereby preventing adhesions. The degradation of the coating may also serve to create pores in the mesh for tissue in-growth. The initiated hydrogel may not undergo the same degradation, thereby maintaining adherence of the mesh to tissue.

In other embodiments, a mesh may be contacted with reactive precursors and initiated precursor(s), the reactive precursors may form a first hydrogel, and the initiated precursor may form a second hydrogel to secure the mesh to tissue. In embodiments, the first hydrogel may form prior to the second hydrogel. In other embodiments the second hydrogel may be formed prior to the first hydrogel. In some embodiments, where the first hydrogel forms prior to the second hydrogel, the first hydrogel may allow for the temporary adherence and placement of the mesh to tissue, permitting repositioning and re-adherence of the mesh to tissue, after which the second hydrogel is formed for permanent placement of the mesh. In such a case, the first hydrogel should remain tacky for adherence and re-adherence of the mesh to tissue for at least 10 minutes, in embodiments from about 10 minutes to about 40 minutes, in embodiments from about 12 minutes to about 25 minutes. After this time, the second hydrogel may be formed.

In embodiments, a mesh implant of the present disclosure may include a filamentous substrate possessing a film coating on at least a portion of the filamentous substrate. In embodiments, the film coating may include a freeze-dried composition including an initiated precursor having at least one vinyl group, in combination with a first hydrogel including a first reactive precursor including a multi-arm polyether possessing electrophilic groups, and a second reactive precursor including nucleophilic groups. In use, the first hydrogel can be re-hydrated to releasably attach the mesh to tissue, and the initiated precursor can be exposed to an initiator to form a second hydrogel securely affixing the mesh to tissue. The first hydrogel may be re-hydrated upon contact with body fluids, the addition of saline, combinations thereof, and the like.

In yet other embodiments, a mixture of reactive and initiated hydrogel precursors may be combined and injected below the surface of tissue and also allowed to pool on the tissue surface. The hydrogel thus formed, both underneath and on the tissue surface, may be contacted with a suture or other medical device. The medical device may then be contacted with the hydrogel anchor, which helps affix the device to tissue. For example, for a suture anchor, the hydrogel may be formed and a suture threaded therethrough. The reactive precursors may form a first hydrogel prior to formation of a second hydrogel from the initiated precursors. In other embodiments, the hydrogel formed from the initiated precursors may be formed prior to the hydrogel formed from the reactive precursors.

In other embodiments, a mixture of reactive and initiated hydrogel precursors may be used to form an implant attachment device such as an anchor or rivet. A mesh or other implant may be secured to tissue by the precursors. The implant may have holes through which the mixture is extruded, similar to the suture anchor described above, i.e., the hydrogel could be injected below the surface of tissue and allowed to pool on the surface of an implant covering the tissue. The reactive hydrogel may then be formed to hold the implant in place and, following implantation, the hydrogel mixture may be exposed to an initiator securing the implant to the tissue.

For example, in embodiments, a mixture may be formed including a first reactive precursor having a multi-arm polyether possessing electrophilic groups, a second reactive precursor having nucleophilic groups, and at least one initiated precursor having at least one vinyl group. A mesh may be contacted with tissue, and the mixture may be injected through the mesh into the tissue. The mixture may form a first hydrogel both underneath and on the tissue surface, in contact with the mesh. The initiated precursor may be contacted with an initiator to form a second hydrogel, thereby forming an attachment device for attaching the mesh to the tissue.

In other embodiments, a composition of the present disclosure may be introduced in situ to form a gastric sleeve. For example, a composition including both reactive and initiated precursors could be applied to the interior of the lumen of the small intestine and stomach at the point where the stomach joins with the small intestine, i.e., at the pylorus. The composition could be applied, in embodiments, endoscopically, with a sprayer or some other applicator suitable for delivery of the composition. The reactive precursors rapidly form the first hydrogel, in embodiments within less than 30 seconds of application, in embodiments from about 5 seconds to about 30 seconds after application, in embodiments from about 10 seconds to about 20 seconds after application. The first hydrogel thus keeps the composition of the present disclosure in the desired location. The initiated precursor is then contacted with an initiator to form the second hydrogel, thereby forming a rigid structure capable of acting as a gastric sleeve. In embodiments, the initiator, whether it be UV, light, chemicals, combinations thereof, and the like, may also be introduced endoscopically. In embodiments, the gastric sleeve may include a cuff, sometimes referred to herein as a retention cuff, at the portion of the stomach adjacent the pylorus, with the remainder of the sleeve formed in the lumen connecting the stomach with the small intestine.

In some embodiments, as described in greater detail below, the precursors utilized to form the gastric sleeve may possess visualization agents, to confirm their placement. Such visualization agents include those visible by X-ray, magnetic resonance imaging (MRI), combinations thereof, and the like.

While the above description has focused on the introduction of the compositions of the present disclosure to produce a gastric sleeve, it should be appreciated that compositions of the present disclosure could be applied to any lumen utilizing similar methods, where additional support for any lumen of any anatomical organ or vessel could benefit from the application of compositions of the present disclosure. For example, utilizing the methods described above for formation of a gastric sleeve, a composition of the present disclosure could be applied endoscopically to the esophagus, small intestine, large intestine, combinations thereof, and the like.

In embodiments, the composition of the present disclosure could be applied vascularly, to the interior of a blood vessel such as a vein, artery, combinations thereof, and the like. For example, the composition of the present disclosure could be applied by way of a catheter to the interior lumen of an artery. In embodiments, the hydrogel precursors could be placed on the external surface of a balloon portion of a balloon catheter for placement on the interior wall of a blood vessel, where they form a gel composition of the present disclosure. In other embodiments, the precursors could be applied and form a gel composition on the surface of the balloon, with the formed gel composition then being applied to the interior wall of a blood vessel. In some embodiments, the precursors and/or gel composition on the balloon could be protected by a retractable cover. In other embodiments, the precursors could be injected over the surface of the balloon at the site for application. In other embodiments, the balloon catheter could possess two balloons, a distal balloon and a proximal balloon, with the precursors introduced onto the wall of a blood vessel in the space between the two balloons. The distal balloon and the proximal balloon thus protect the precursors from the blood and any premature gelling.

Once applied to the blood vessel wall, the reactive precursors rapidly form the first hydrogel, in embodiments within less than 30 seconds of application, in embodiments from about 5 seconds to about 30 seconds after application, in embodiments from about 10 seconds to about 20 seconds after application. The first hydrogel thus keeps the composition of the present disclosure in the desired location. The initiated precursor is then contacted with an initiator to form the second hydrogel, thereby forming a rigid structure. In embodiments, this rigid structure is capable of acting as a stent. In embodiments, the initiator, whether it by UV, light, chemicals, combinations thereof, and the like, may also be introduced from the balloon catheter. For example, in embodiments, the balloon may be transparent to UV light and may possess a UV source. The balloon may be expanded to assist in holding the precursors against the vessel lumen, and UV light may then be applied to the precursors through the balloon to initiate the initiated precursors, thereby forming the second hydrogel.

In embodiments, the balloon could possess a pattern, sometimes referred to herein as a mask, that does not permit transmission of UV light, thereby permitting the formation of a stent having selective cross-linked, hardened, portions.

As noted above, in embodiments, the hydrogel precursor(s) and/or the resulting hydrogel may contain visualization agents to improve their visibility during surgical procedures. Visualization agents may be selected from a variety of non-toxic colored substances, such as dyes, suitable for use in implantable medical devices. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include, for example, FD&C Blue #1, FD&C Blue #2, FD&C Blue #3, FD&C Blue #6, D&C Green #6, methylene blue, indocyanine green, other colored dyes, and combinations thereof. It is envisioned that additional visualization agents may be used such as fluorescent compounds (e.g., fluorescein or eosin), x-ray contrast agents (e.g., iodinated compounds), ultrasonic contrast agents, and MRI contrast agents (e.g., Gadolinium containing compounds).

The visualization agent may be present in a hydrogel precursor solution. The colored substance may or may not become incorporated into the resulting hydrogel.

The visualization agent may be used in small quantities, in embodiments less than 1% weight/volume; in embodiments less that 0.01% weight/volume; and in embodiments less than 0.001% weight/volume concentration.

Hydrogel precursors, as well as their reaction products, may also be used for drug therapy or delivery of bioactive agents. In embodiments, the hydrogel may be coated with or include additional bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent, which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the hydrogel in any suitable form of matter, e.g., films, powders, liquids, gels and the like.

As noted above, in embodiments that include a multi-arm PEG or PEG star, the bioactive agent may be incorporated into the core of the PEG, the arms of the PEG, or combinations thereof. In embodiments, the bioactive agent may be attached to a reactive group in the PEG chain. The bioactive agent may be bound covalently, non-covalently, i.e., electrostatically, through a thiol-mediated or peptide-mediated bond, or using biotin-adivin chemistries and the like.

Examples of classes of bioactive agents which may be utilized in accordance with the present disclosure, include, for example anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the hydrogel, in embodiments a hydrogel implant, and surrounding tissues. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents, which may be included as a bioactive agent include: triclosan, also known as 2,4,4'- trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides, such as tobramycin and gentamicin, rifampicin, bacitracin, neomycin, chloramphenicol, and miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anticonvulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins; cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the hydrogel include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

The bioactive agent may be released from the hydrogel as a bolus, over a period of time, or combinations thereof. The reactive precursors may form a hydrogel that is more permeable, allowing diffusion of a bioactive agent from the hydrogel. In embodiments, the initiated precursor may be crosslinked to form a barrier layer over the hydrogel formed from the reactive precursors, thereby, reducing diffusion of a bioactive agent therefrom.

Figure 1B:
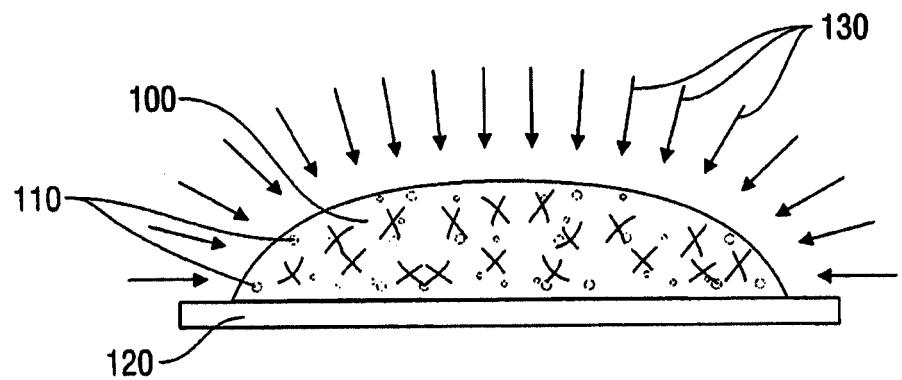
FIG. 1B is a cross-sectional view of the hydrogel of FIG. 1A depicting exposure to an initiator.
Figure 1C:
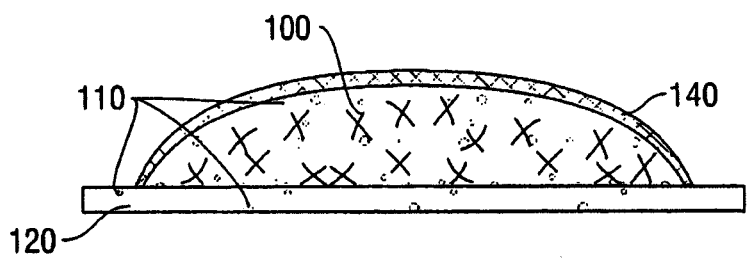
FIG. 1C is a cross-sectional view of the hydrogel of FIG. 1A following exposure to an initiator.

Embodiments of the present disclosure will now be described with reference to the figures. With reference to FIG. 1A, reactive precursors crosslink to form a hydrogel 100, optionally containing a bioactive agent 110 on tissue 120 in situ. As shown in FIG. 1B, the hydrogel 100 may then be exposed to an initiator 130 such as UV light to initiate reaction of initiated precursor(s) included therein. FIG. 1C shows formation of a barrier layer 140 on hydrogel 100, which is formed by the initiated precursor(s) and inhibits diffusion of the bioactive agent 110 from the hydrogel. Thus, the bioactive agent 110 may diffuse unidirectionally into the tissue 120 in need of the bioactive agent 110, but not diffuse into any lumen or area adjacent tissue 120 due to the presence of barrier layer 140. Unidirectional distribution of a bioactive agent may be used, for example, for direct delivery of chemotherapeutic agents to dura, lung, or bowel; anti-clotting drugs to cardiovascular tissues; anti-arrhythmia drugs to the heart; anti-inflammatories or analgesics to wounded tissues; hemostats to treat wounded tissue; and the like, and combinations of these.

As shown in FIG. 2A, a hydrogel 200 may be formed from reactive precursors in the shape of a spinal disc. FIG. 2B is a side view of the hydrogel 200, which may be exposed to an initiator 220 to gel any initiated precursors within hydrogel 200. FIG. 2C is a cross-sectional view of the resulting disc having a hydrogel 200 formed from reactive precursors and a denser barrier layer 230 formed from initiated precursors. The reaction of the initiated precursors may increase the density of the surface area, thereby creating a "skin" or barrier of denser hydrogel 230 on the surface of hydrogel 200. In such a manner, an implant such as a non-degradable vertebral disc replacement may be formed.

In embodiments, a two-phase hydrogel implant may be formed. For example, the two-phase hydrogel implant may be formed using a template and/or a screen. The template and screen(s) may be any shape or size. In embodiments, the template may be a cylinder having a base (similar to a laboratory beaker) and the screens may include a series of circular discs of various sizes. Utilizing the template and screens, a dense bottom layer, a middle layer, and a dense top layer may be formed with the template and screen(s). For example, a dense bottom layer may be formed by applying the reactive and initiated hydrogel precursors to the base of the template, allowing the reactive precursors to form a hydrogel, and then exposing the hydrogel to an initiator to crosslink the initiated precursor(s) thereby forming a dense bottom layer. A middle layer may then be formed on top of the bottom layer, by applying reactive precursors thereto, optionally with initiated precursors, and allowing them to react. A dense top layer may then be formed, for example, by applying a screen to the middle layer and then applying both reactive and initiated hydrogel precursors to the middle layer, and allowing the reactive precursors to form a hydrogel layer. The top hydrogel may then be exposed to an initiator to crosslink the initiated precursor(s) in the top hydrogel to form a dense top layer. The screen will prevent crosslinking of any initiated precursors in the middle layer. The screen may remain or, in embodiments, the screen may be removed. Thus, the resulting gel will have a denser top layer and a denser bottom layer, and a less dense middle layer.

Each of the layers formed may contain the same or different hydrogel precursors. Additionally, each of the layers may contain a bioactive agent. The type and quantity of bioactive agent in each layer may be the same or different.

Figure 3A:
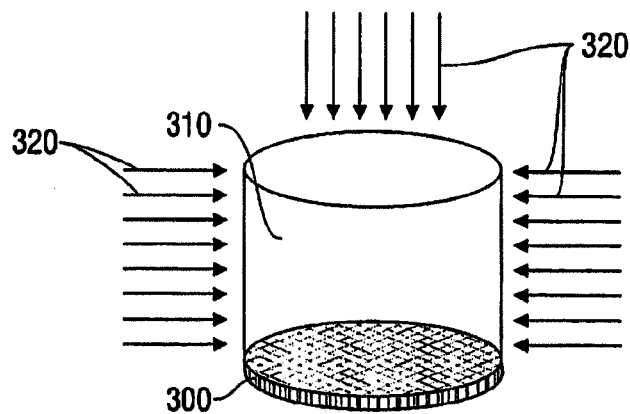
FIG. 3A is a side view of a template used during formation of a hydrogel of the present disclosure.
Figure 3B:
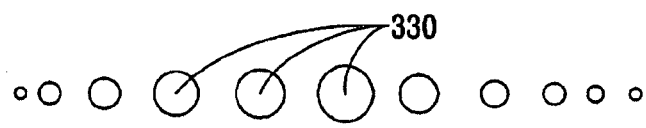
FIG. 3B is an elevated view of a blocking device or screen for use with a template in accordance with the present disclosure.
Figure 3C:
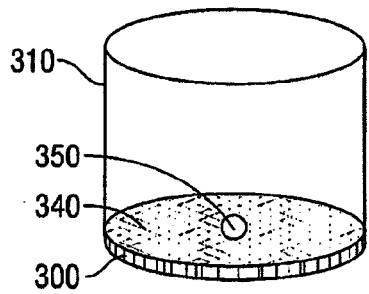
FIG. 3C is a side view of a template and blocking device used in accordance with the present disclosure.
Figure 3D:
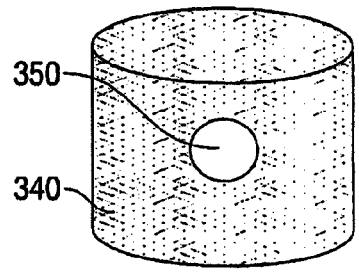
FIG. 3D is a side view of a hydrogel implant of the present disclosure.

A method of forming a two-phase drug delivery hydrogel implant is further described with reference to FIG. 3. As shown in FIG. 3, a layer of hydrogel precursors is placed in template 310. The reactive precursors form a hydrogel 300 upon exposure to each other. The initiated hydrogel precursors are exposed to an initiator 320 to increase their crosslinking, thereby forming a dense bottom layer. FIG. 3B shows several screens 330 of varying sizes. A screen 330 may be placed on hydrogel 300. Additional precursors may then be added on top of hydrogel 300, allowed to react, and optionally exposed to the initiator 320 to form the next layer (not shown). This process may be repeated to create a densely crosslinked gel with a core that is less dense, due to the presence of the screens, which block the exposure of the precursors to the initiator. As shown in FIG. 3C, the center 350 that was screened may remain less dense than the portion of hydrogel 340 not covered by the screens. In embodiments, screens 330 of different sizes and/shapes may be used to form different centers. The resulting two-phase drug delivery hydrogel implant 340 may thus include a more dense hydrogel 340 with a less dense hydrogel 350 forming a center portion.

Upon placement in situ, the center hydrogel portion 350 of the two-phase drug delivery hydrogel may degrade at a rate that is faster than that of the denser hydrogel 340. The slower degradation rate of the denser hydrogel 340 may thus provide for a gradual release of a bioactive agent over time, with additional release from the less dense center 350 as a bolus upon degradation of hydrogel 340. In other embodiments, the center hydrogel may degrade slower than the surrounding hydrogel allowing for a bolus delivery followed by a slow release maintenance dosage. This may prove beneficial for extended release applications. Immediate/extended release drug delivery systems may be useful for application for example in delivery of narcotics, anticoagulants, anti-inflammatories, chemotherapeutics, peptides, growth factors, combinations thereof, and the like.

Figure 5A:
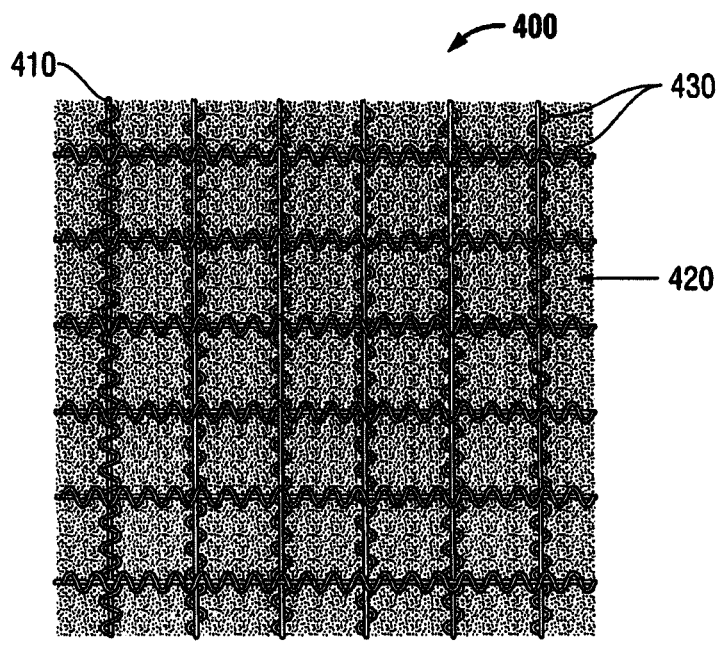
FIG. 5A is an elevated view of a mesh implant having a coating including the hydrogel of the present disclosure.
Figure 5B:
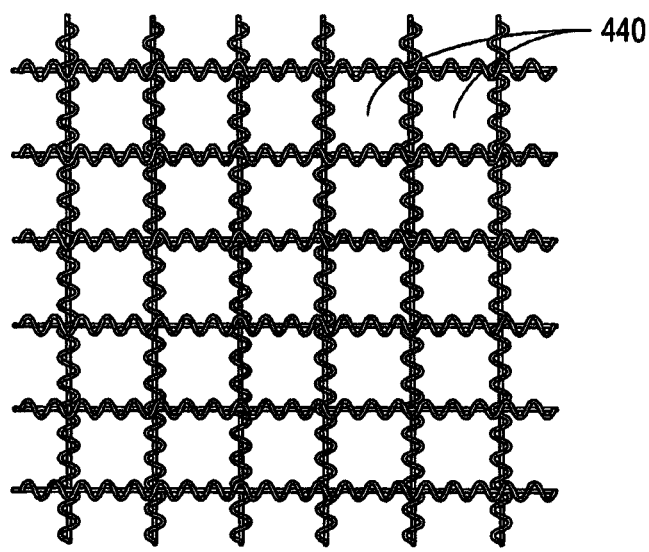
FIG. 5B is an elevated view of the implant of FIG. 5A following degradation of a portion of the hydrogel of the disclosure.

Another use of a hydrogel according to the present disclosure to form an implant is depicted in FIGS. 5A and 5B. The implant 400 includes a mesh 410. The mesh 410 may be coated with an initiator such as permanganate/acetic acid, ammonium persulfate/acetic acid, potassium persulfate/2,2'-azobis[2-(2-dimidazolin-2-yl)propane]dihydrochloride (2,2'-azobis[2-(2-dimidazolin-2-yl)propane]dihydrochloride is commercially available as VA044 (Wako), ammonium persulfate/tetramethylenediamine, combinations thereof, and the like. A mixture of an electrophilic reactive precursor and an initiated precursor such as PEG-NHS and PEG-acrylate 420 may be sprayed onto the mesh 410. The entire mesh 410 may then be coated with a nucleophilic reactive precursor such as trilysine and additional initiated precursor such as unreacted acrylate. The PEG-acrylate contacting the mesh 410 may be initiated by the permanganate/acetic acid in the mesh and crosslink 430. The PEG-NHS and trilysine may also react to form a less densely cross-linked hydrogel 420 across the surface of the entire mesh, including the pores of the mesh 410. As depicted in FIG. 5B, the PEG-NHS-trilysine hydrogel 420 may degrade over a period of time of from about 4 days to about 6 days, exposing pores 440 of the mesh 410 thereby allowing space for tissue in-growth. Such a mesh could be used, for example, in hernia repair.

Figure 6A:
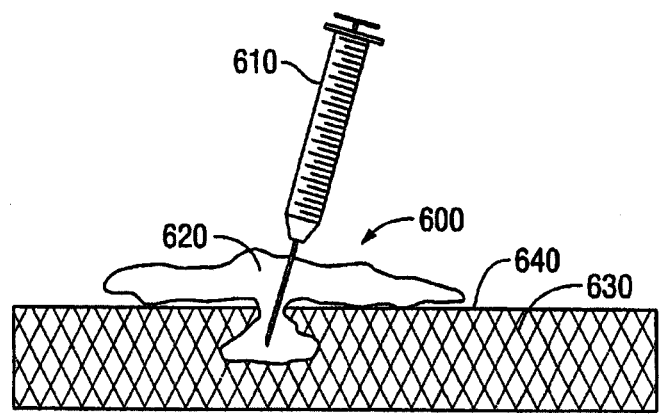
FIG. 6A is a cross-sectional view of a suture anchor formed using the hydrogel of the present disclosure.
Figure 6B:
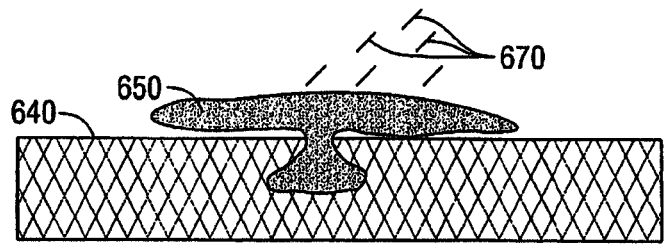
FIG. 6B is a cross-sectional view of the suture anchor of FIG. 6A depicting cross-linking of the initiated precursor.
Figure 6C:
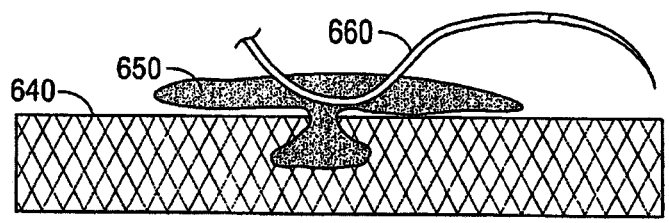
FIG. 6C is a cross-sectional view of the suture anchor of FIG. 6A after cross-linking of the initiated precursor.

In other embodiments, as shown in FIG. 6A, the hydrogel of the disclosure may be utilized to form a suture anchor 600. A syringe 610 may inject a mixture 620 of electrophilic and nucleophilic (reactive) hydrogel precursors and an initiated hydrogel precursor beneath tissue 630 to form a soft hydrogel 620 both underneath and on the surface 640 of the tissue 630. As shown in FIG. 6B, the soft hydrogel 620 may be initiated with UV light 670 to create a densely cross-linked suture anchor 650. As shown in FIG. 6C, suture 660 may then be passed through suture anchor 650. Such a suture anchor could be used for example, for in situ wound closure, bone anchor, tendon repair, combinations thereof, and the like.

In other embodiments, not shown, one could first initiate the initiated hydrogel precursor, and then allow the reactive precursors to react after formation of the initiated hydrogel.

Figure 7A:
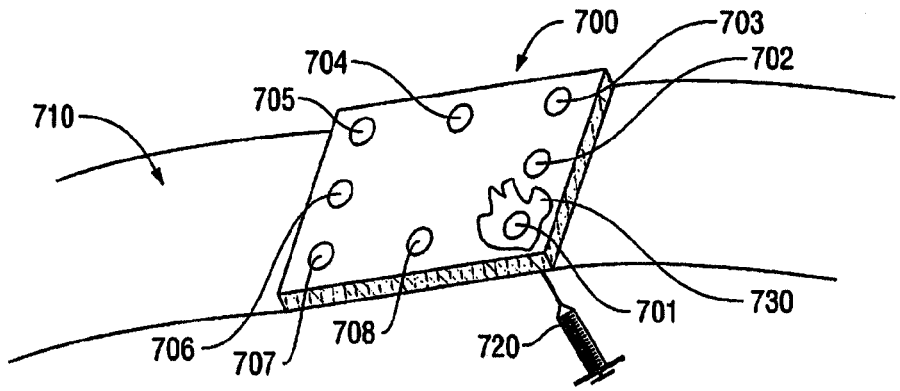
FIG. 7A is an elevated view of an implant for adherence to tissue using the hydrogel of the present disclosure.
Figure 7B:
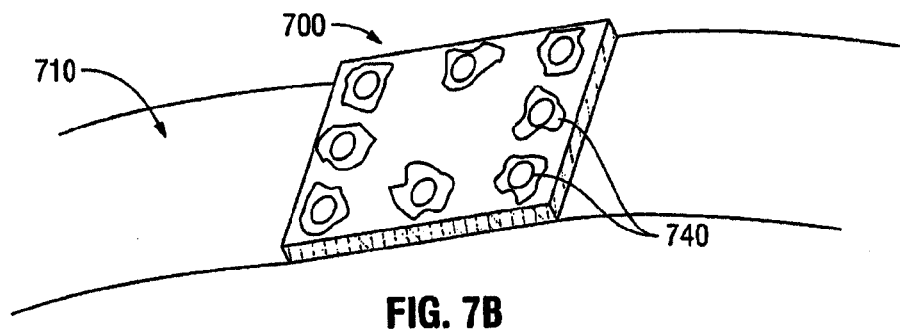
FIG. 7B is an elevated view of the implant of FIG. 7A prior to cross-linking of the initiated precursor.
Figure 7C:
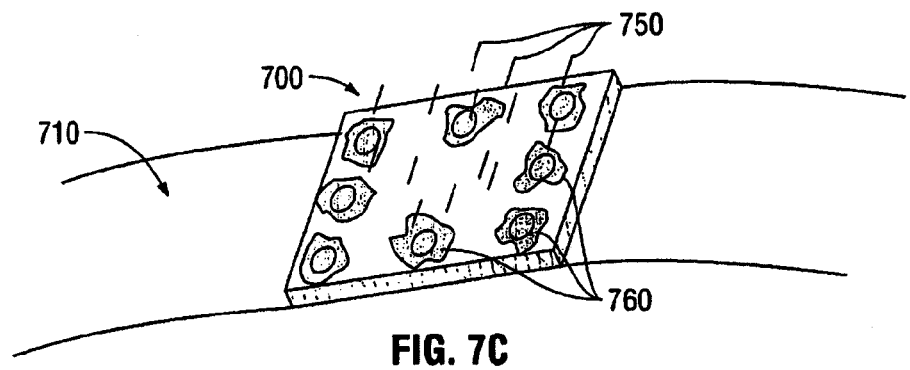
FIG. 7C is an elevated view of the implant of FIG. 7A following cross-linking of the initiated precursor.

In yet other embodiments, a rivet may be formed from the hydrogel of the disclosure to adhere an implant to tissue as shown in FIGS. 7A-C. An implant 700 may be applied to the peritoneum 710 for hernia correction. A syringe 720 may be used to inject a hydrogel mixture 730 from beneath the peritoneum 710 (or from above, not shown) through holes 701, 702, 703, 704, 705, 706, 707, and 708 of the implant 700. The hydrogel mixture 730 may form a soft hydrogel 740 below the peritoneum, filling holes 701, 702, 703, 704, 705, 706, 707, and 708, and pooling slightly on the non-tissue side of the implant 700. The soft hydrogel 740 may then be exposed to an initiator 750 to form a densely cross-linked hydrogel rivet 760, thereby adhering the implant 700 to the peritoneum 710.

Figure 10:
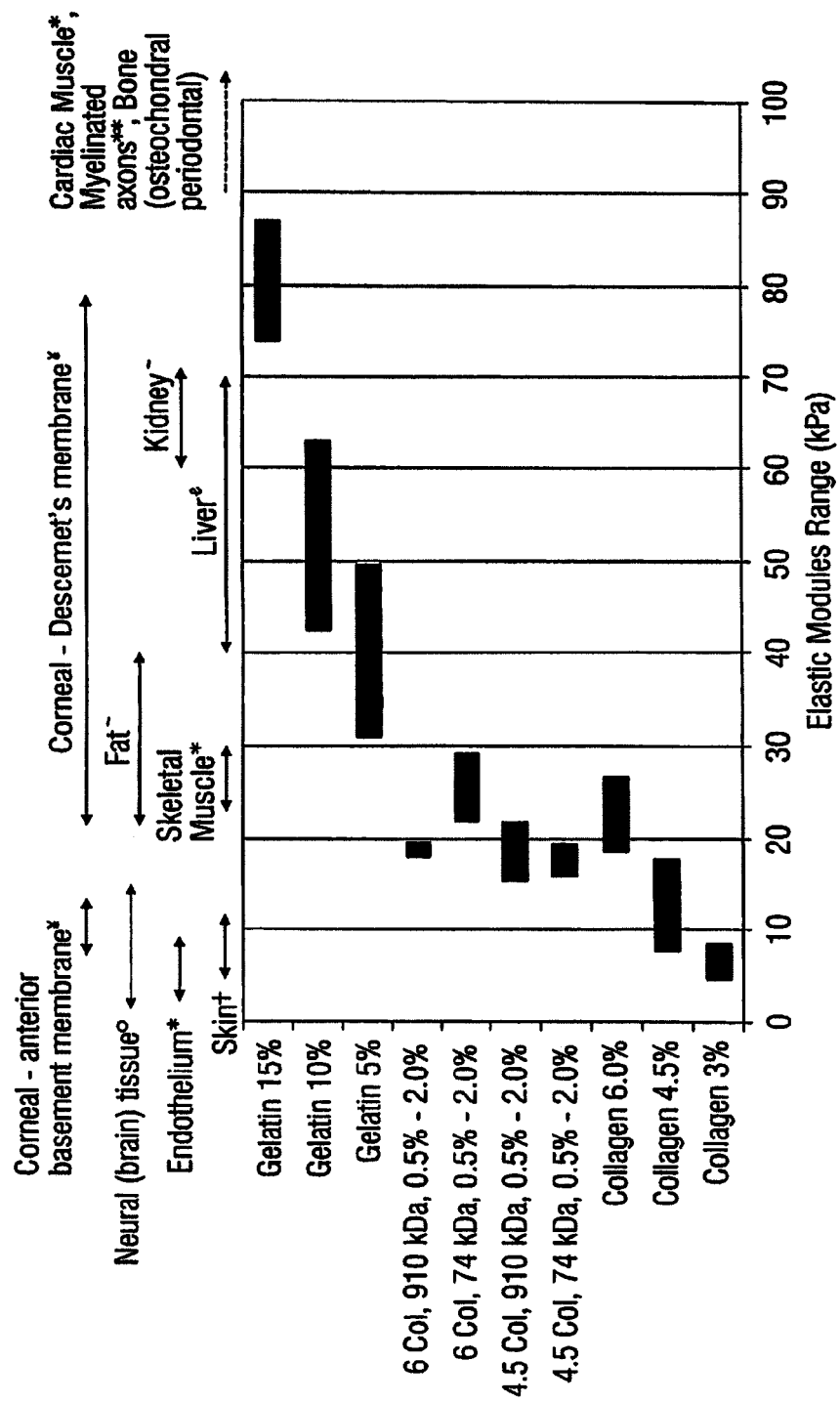
FIG. 10 is a graph depicting the elastic modulus of different tissues and other materials, including collagen and gelatin.

As noted above, in embodiments a hydrogel composition of the present disclosure may have varying modulus. One skilled in the art, in embodiments, may tailor the components utilized to form a composition of the present disclosure based upon the tissue to which the composition is to be applied. FIG. 10 provides the elastic modulus for various tissues, which may be utilized as a guide in preparing a composition of the present disclosure having a desired modulus.

Figure 11:
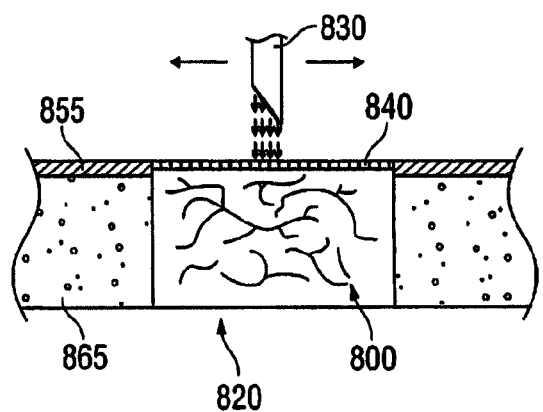
FIG. 11 is a depiction of a use of a composition of the present disclosure to repair a defect in tissue.

In embodiments, as depicted in FIG. 11, a hydrogel composition may be utilized to fix a defect in tissue. FIG. 11 depicts the use of a composition of the present disclosure to repair a defect in subchondral bone. The reactive precursors and initiated precursor may be applied to a defect 820 in subchondral bone 865, thereby forming a first hydrogel 800 therein. A source of radiation 830 may be applied to the surface of hydrogel 800 adjacent articular cartilage 855 surrounding the defect, thereby forming a second hydrogel on the surface which functions as a barrier layer 840.

Figure 12A:
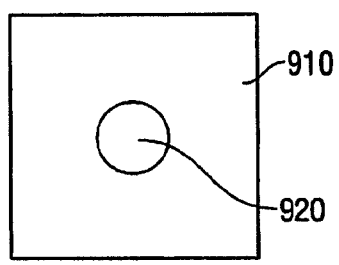
FIG. 12A is a view of an implant including a composition of the present disclosure, having a disperse region formed of one hydrogel within a second hydrogel.
Figure 12B:
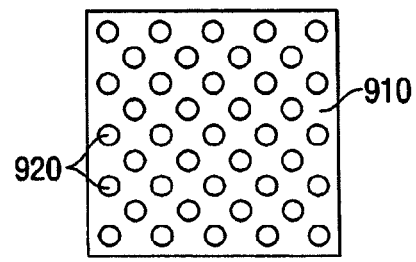
FIG. 12B is an alternate view of an implant including a composition of the present disclosure, having disperse regions formed of one hydrogel within a second hydrogel.

As noted above, in embodiments a hydrogel composition of the present disclosure may include one hydrogel dispersed in a second hydrogel. As depicted in FIG. 12A, a disperse region 920 may include a core formed of a second hydrogel formed of an initiated precursor within a first hydrogel 910 formed of reactive precursors. Alternatively, as depicted in FIG. 12B, many disperse regions 920 may be formed within the first hydrogel 910. While not depicted in FIGS. 12A and 12B, in some embodiments a barrier layer formed from initiated precursors may be formed over the hydrogel composition of the present disclosure.

Figure 13:
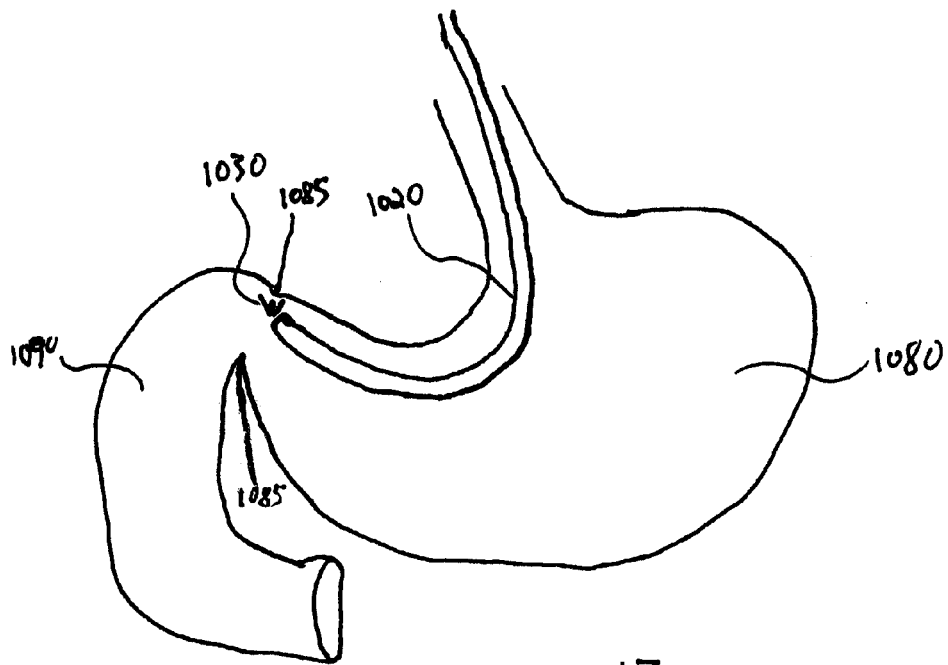
FIG. 13 is a cross-sectional view showing the endoscopic application of a composition of the present disclosure to the gastrointestinal region where the stomach meets the small intestine.
Figures 14A, 14B, 14C:
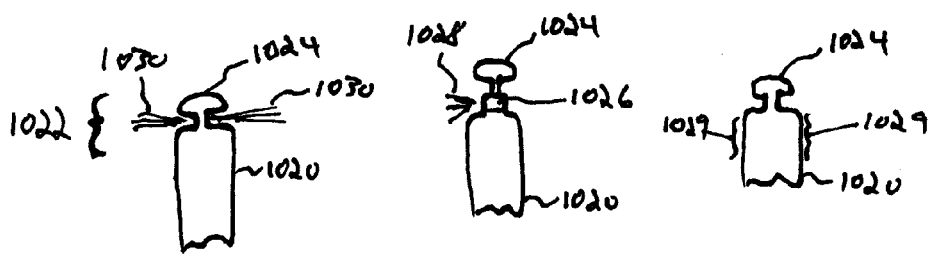
FIG. 14A is a side view of a distal tip of an endoscope showing the dispensing of precursors.
FIG. 14B is a side view of a distal tip of an endoscope showing the emission of UV light as an initiator.
FIG. 14C is a side view of a distal tip of an endoscope showing the emission of ultrasound as an initiator.
Figure 15:
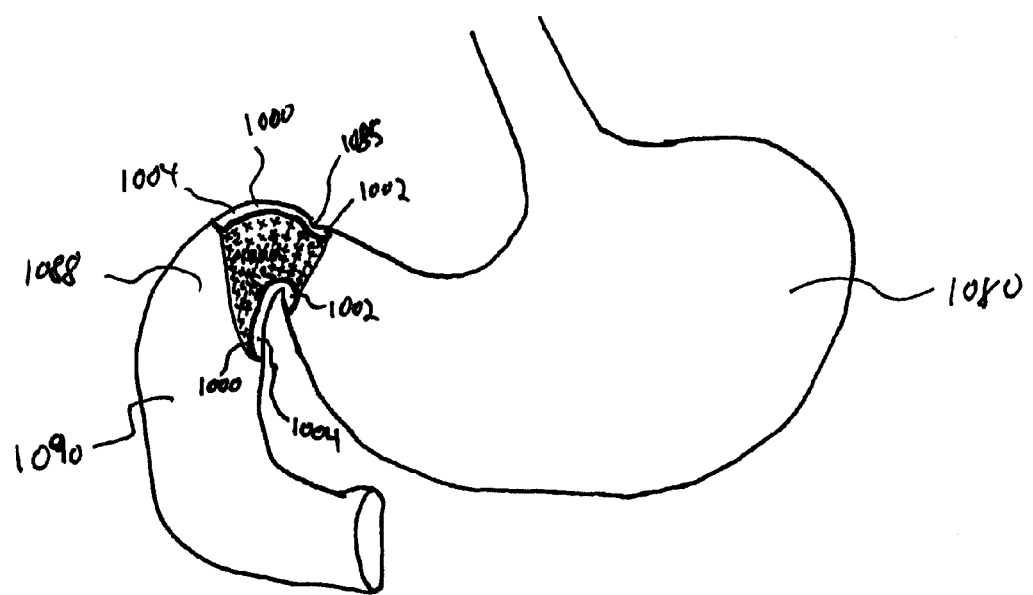
FIG. 15 is a cross-sectional view of a gastric sleeve formed of a composition of the present disclosure.

Examples of how gastric sleeves may be formed, including devices used for their formation, are set forth in FIGS. 13-15. FIG. 13 shows the introduction of an endoscope 1020 into stomach 1080, for deposition of precursors 1030 in the region of the pylorus 1085 between stomach 1080 and small intestine 1090. Various applicators may be included at the distal end of endoscope 1020 for delivery of the precursors and/or initiators. For example, as depicted in FIG. 14A, distal end 1022 of endoscope 1020 may possess a cap 1024 that may be extended, permitting the lateral expulsion of precursors 1030 onto the walls of the lumen of stomach 1080 and small intestine 1090 adjacent the pylorus 1085. As depicted in FIG. 14B, the same or different endoscope may possess an ultraviolet (UV) light source 1026, capable of laterally emitting UV light 1028 to initiate the initiated precursors. (While not shown, in embodiments, chemical initiators may be laterally emitted using the same endoscope depicted in FIG. 14A, with the chemical initiator introduced in the same fashion as the precursors.) Other initiating systems include those depicted in FIG. 14C, which shows an endoscope 1030 capable of emitting ultrasound 1029 for initiating the initiated precursors.

Once formed, as depicted in FIG. 15, the gastric sleeve 1000 may possess a retention cuff 1002 in the stomach 1080, with sleeve 1004 extending past the pylorus 1085 into the lumen 1088 of small intestine 1090.

Figure 16:
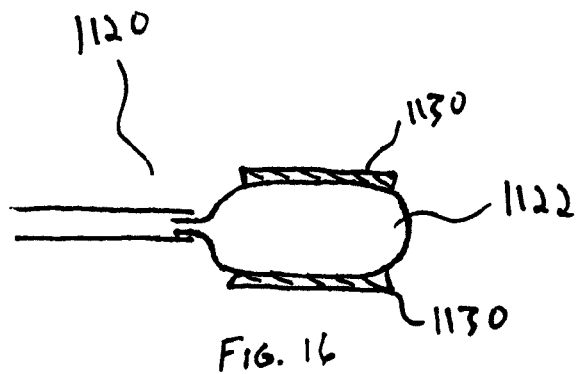
FIG. 16 is a side view of a balloon catheter having precursors of a composition of the present disclosure on a surface thereof for application to the internal wall of a body lumen.
Figure 17:
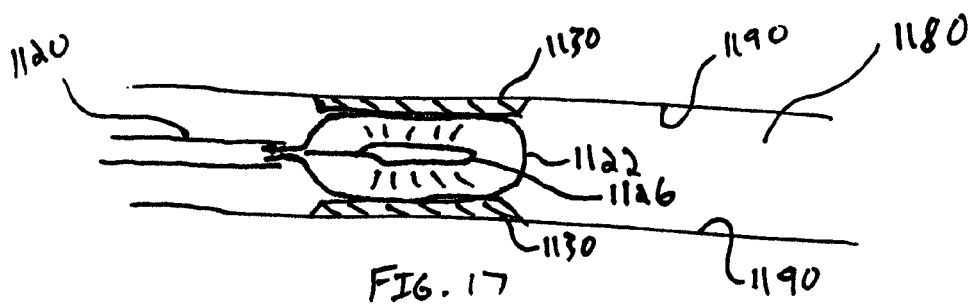
FIG. 17 is a side view of a balloon catheter within a blood vessel, applying a composition of the present disclosure to the internal wall of a blood vessel.
Figure 18:
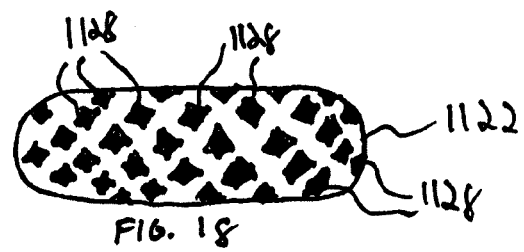
FIG. 18 is a side view of a balloon having a mask thereon that selectively permits transmission of an initiator such as UV light.
Figure 19:
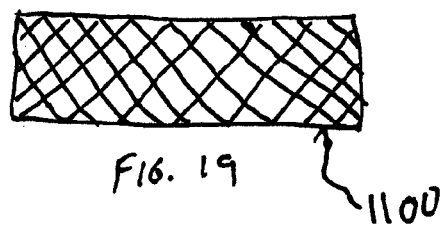
FIG. 19 is a side view of a stent formed of a composition of the present disclosure.

Examples of how a composition of the present disclosure may be applied to an internal wall of a blood vessel are set forth in FIGS. 16-20. FIG. 16 shows a catheter 1120 including balloon 1122 having a composition 1130 including both reactive and initiated precursors located on the surface thereof. FIG. 17 shows the introduction of a catheter 1120 into a blood vessel 1180, for deposition of composition 1130 on a portion of internal wall 1190 of vessel 1180. FIG. 17 also depicts balloon 1122 having a UV light source 1126 within balloon 1122 for initiating the initiated precursors included in composition 1130. FIG. 18 depicts a balloon 1122 possessing a pattern 1128 that does not permit transmission of UV light. As depicted in FIG. 19, upon initiating the initiated precursors with UV light, the pattern results in formation of a stent 1100 having selective cross-linked, hardened, portions corresponding to the pattern 1128 on balloon 1122.

Figure 20:
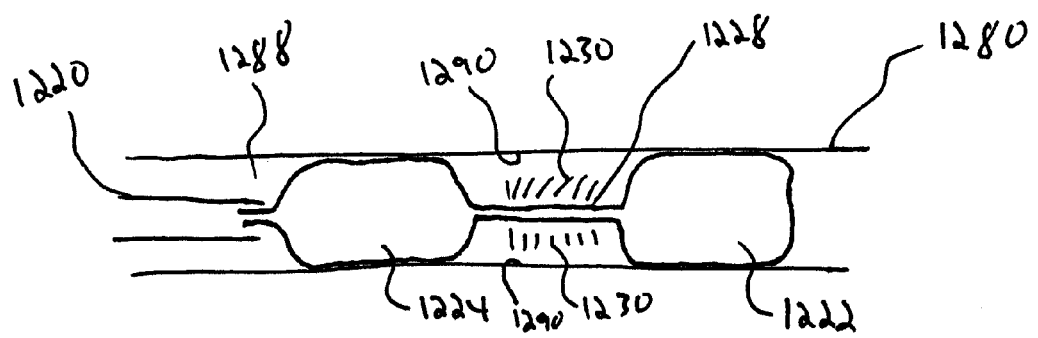
FIG. 20 is a side view of an alternate balloon catheter for use in administering a composition of the present disclosure.

FIG. 20 depicts a balloon catheter 1220 within lumen 1288 of blood vessel 1280, possessing two balloons, a distal balloon 1222 and a proximal balloon 1224. Composition 1230, including the reactive and initiated precursors, may be introduced onto the wall 1290 of blood vessel 1280 from segment 1228 of catheter 1220 located in the space between the distal balloon 1222 and proximal balloon 1224. Once the precursors are applied to the wall of the vessel, an initiator may be applied using any of the above described means.

A bioactive agent may be included in the first hydrogel, the second hydrogel, or both. The bioactive agent, in embodiments, may be in liposomes, microspheres, microbubbles, combinations thereof, and the like. Where a bioactive agent is present in the first and second hydrogels, the same or difference bioactive agent may be included in the hydrogels. The bioactive agent may be released from the first hydrogel over a period from about 1 day to about 6 weeks, in embodiments from about 1 week to about 4 weeks, and the bioactive agent may be released from the second hydrogel over a period from about 5 days to about 12 weeks, in embodiments from about 2 weeks to about 8 weeks.

Examples of compositions including hydrogels with multiple release profiles include those disclosed in U.S. Patent Application Publication No. 2009/0047349, the entire disclosure of which is incorporated by reference herein.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 30° C.

EXAMPLES

Example 1

Solution Preparation

First Reactive Precursor: An 80% solution of PEG-diacrylate in phosphate buffer pH 4.04 was prepared. PEG-NHS was added to this solution at a concentration of 0.13 g/ml (0.39 grams of PEG-NHS in 3 ml of 80% diacrylate in phosphate buffer).

Second Reactive Precursor: A 0.01 g/ml solution of lysine in borate buffer was prepared and the pH was adjusted to 8.6.

Initiated Precursor: A 10 mg/ml solution of 4,4'-bis(diethyl-amino)benzophenone (excitation wavelength of 365 nm) in ethanol was prepared.

Varying amounts of Initiated Precursor solution were added to the First Reactive Precursor as delineated in Table 2 (below).

Reaction of First and Second Reactive Precursors

Equal volumes of First and Second Reactive Precursors were loaded into separate syringes. The syringes were connected and the solutions were mixed for 15 seconds. Next the solutions sat for 15 minutes in order to ensure complete crosslinking of the hydrogel.

Crosslinking of Initiated Precursor

Each crosslinked hydrogel was then removed from its respective syringe and cut into several cylinders. The crosslinked hydrogel was then exposed to varying amounts of UV light (see Table 2) to initiate crosslinking of the initiated precursor to form an initiated hydrogel. The cylinder of gel was skewered with a long needle, placed under the UV source, and rotated to allow for even curing.

Hydrogel Composition Testing

Figure 8:
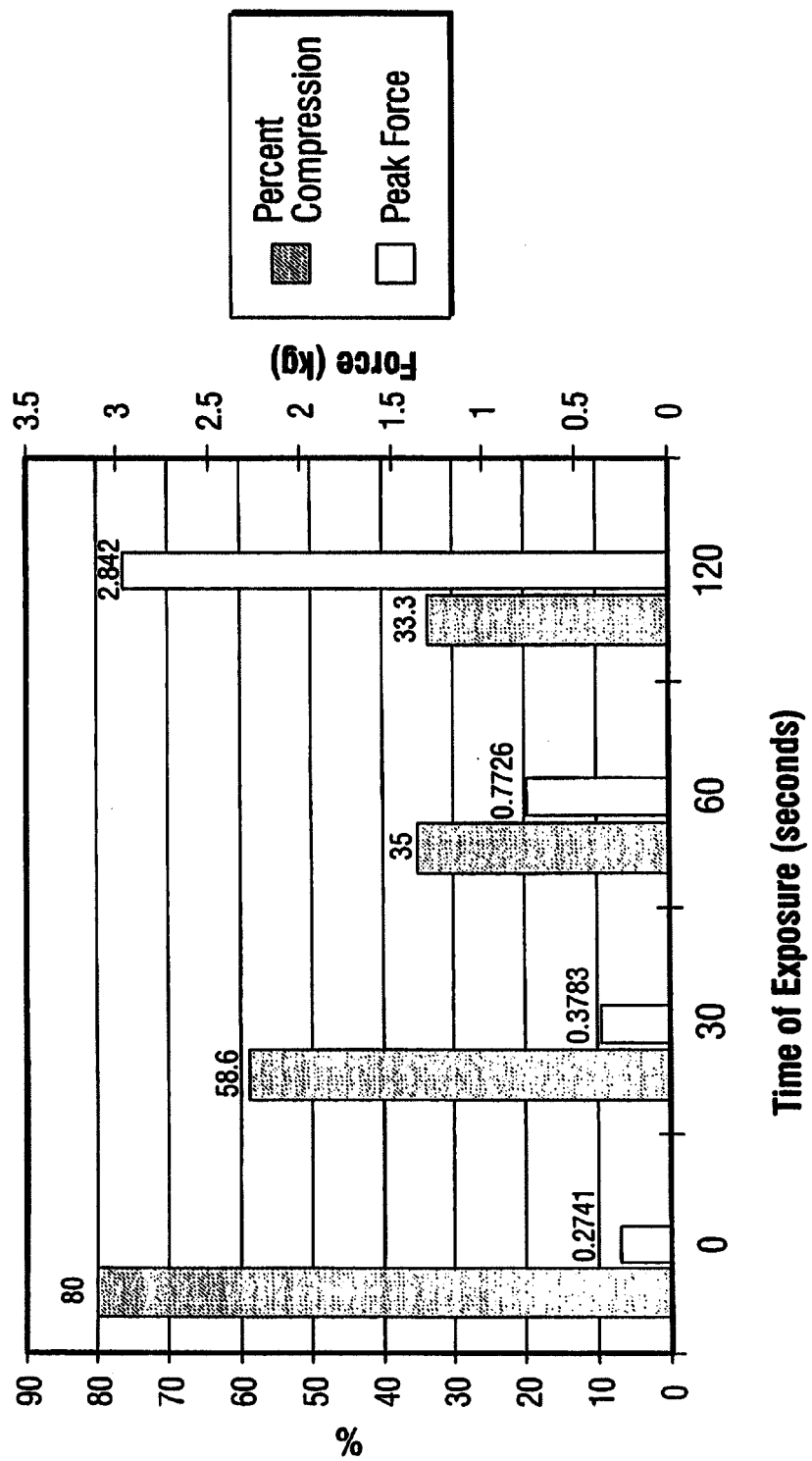
FIG. 8 is a graph of the data presented in Table 2.
Figure 9:
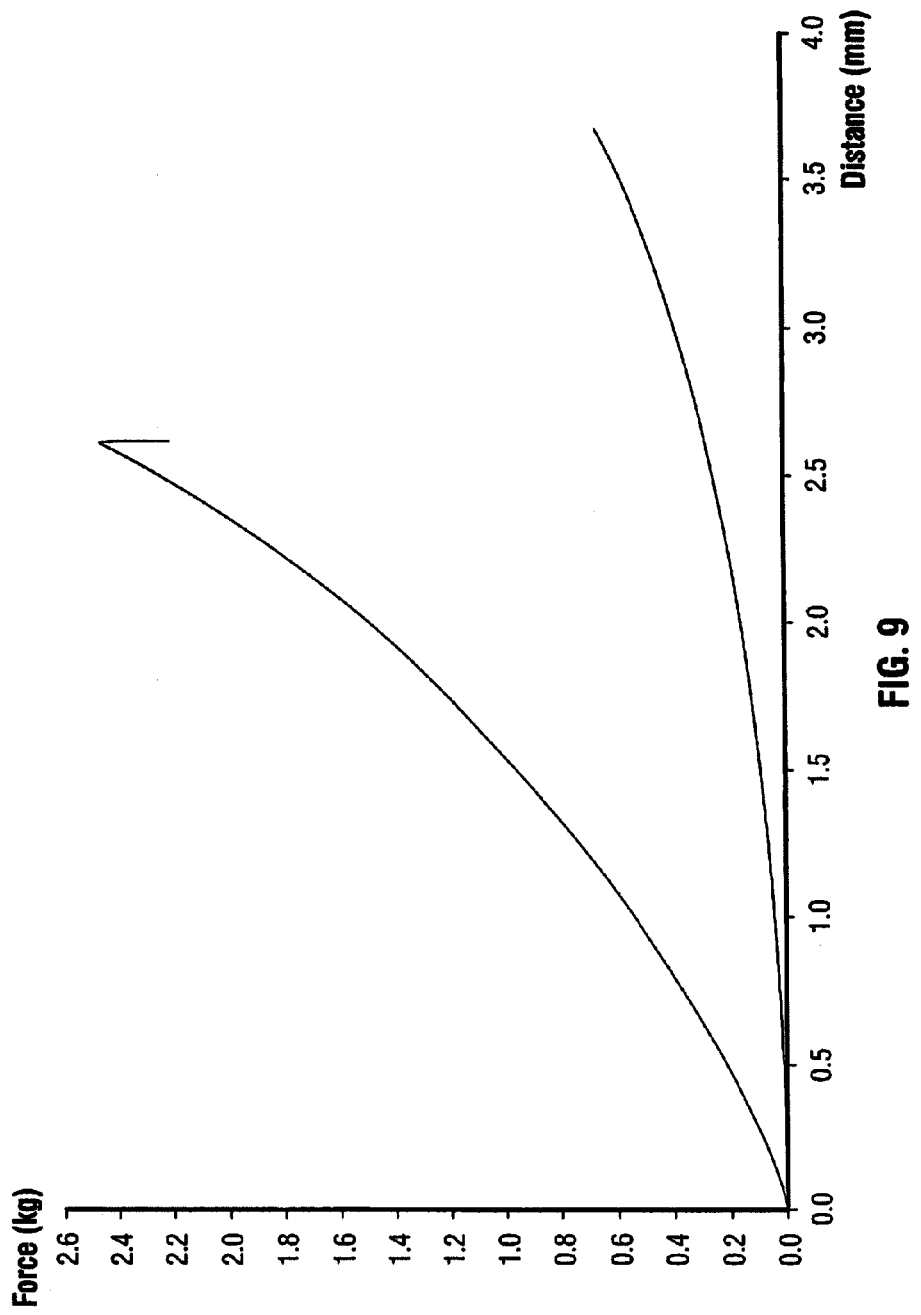
FIG. 9 is a graph comparing force applied and amount of compression for an initiated hydrogel and an uninitiated hydrogel.

Once the cylinders were cured, each was placed under a 12 mm flat probe and compressed to a maximum of 80% of its initial height, or until breaking, at a rate of 0.08 mm/sec with a trigger force of 20 grams and a break sensitivity of 5 grams. Results for each cured hydrogel are recorded in Table 2. FIG. 8 is a bar graph showing the data of Table 2 (the sample with 100 microliters of photoinitiator). FIG. 9 is a comparison of the initiated hydrogel (top line) and uninitiated hydrogel (bottom line).

TABLE 2

| Microliters of Initiated Precursor | Time (seconds) Of UV Exposure | % Compression | Max Force in grams (g) |
| --- | --- | --- | --- |
| 15 | 0 | 80.0 | 275.60 |
|  | 30 | 49.1 | 541.70 |
|  | 60 | 34.8 | 2607.00 |
|  | 120 | 42.5 | 12,187.40 |
| 25 | 0 | 80.0 | 221.90 |
|  | 30 | 78.6 | 827.00 |
|  | 60 | 40.3 | 3447.10 |
|  | 120 | 52.6 | 16,911.00 |
| 25 | 0 |  | 258.80 |
|  | 30 | 40.6 | 362.60 |
|  | 60 | 33.2 | 2140.50 |
|  | 120 | 52.2 | 16,304.90 |
| 50 | 0 | 80.0 | 308.60 |
|  | 30 | 67.0 | 1144.50 |
|  | 60 | 34.9 | 1900.60 |
|  | 120 | 52.1 | 14,567.50 |
| 100 | 0 | 80.0 | 274.10 |
|  | 30 | 58.6 | 378.30 |
|  | 60 | 35.0 | 772.60 |
|  | 120 | 33.3 | 2942.60 |

Example 2

The preparation of Example 1 was repeated using trilysine in place of the lysine in the Second Hydrogel Precursor. Results of the testing are provided in Table 3 below.

TABLE 3

| Microliters of Initiated Precursor | Time (seconds) of UV Exposure | % Compression | Max Force (g) |
|---|---|---|---|
| 25 | 0 | 79.7 | 511.00 |
|  | 30 | 47.5 | 613.00 |
|  | 60 | 33.1 | 2632.30 |
|  | 120 | 44.3 | 11,726.00 |
| 50 | 0 | 72.9 | 605.15 |
|  | 60 | 33.9 | 1399.40 |
|  | 120 | 50.1 | 15,987.10 |

As shown by the above Examples, various degrees of crosslinking were achieved by varying the amount of initiated precursor and the amount of UV exposure of the initiator. Additionally, depending on the first and second hydrogel precursor used, varying levels of crosslinking prior to exposure to UV was achieved.

The above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed:

1. A kit comprising:
    a first reactive precursor comprising electrophilic groups, a second reactive precursor comprising nucleophilic groups, and a separate initiated precursor comprising at least one vinyl group;
    an initiator to initiate crosslinking of the separate initiated precursor; and
    a device for introducing the first reactive precursor, the second reactive precursor, the separate initiated precursor, and the initiator to a body lumen.

2. The kit of claim 1, further comprising an initiator mask to selectively expose the separate initiated precursor to the initiator.

3. The kit of claim 1, wherein the first reactive precursor, the second reactive precursor, or both, comprise a core comprising a component selected from the group consisting of polyethylene glycol, polyethylene oxide, polyethylene oxide-co-polypropylene oxide, co-polyethylene oxide block copolymers, co-polyethylene oxide random copolymers, polyvinyl alcohol, poly(vinyl pyrrolidinone), poly(amino acids), dextran, chitosan, alginates, carboxymethylcellulose, oxidized cellulose, hydroxyethylcellulose, hydroxymethylcellulose, hyaluronic acid, albumin, collagen, casein, gelatin, and combinations thereof.

4. The kit of claim 1, wherein the first reactive precursor possesses N-hydroxysuccinimide groups and the second reactive precursor possesses amine groups.

5. The kit of claim 1, wherein the separate initiated precursor is selected from the group consisting of acrylic acid, methacrylic acid, phosphorylcholine containing monomers, furanone functional vinyl monomers, potassium sulfopropyl acrylate, potassium sulfopropyl methacrylate, n-vinyl pyrrolidone, hydroxyethyl methacrylate, vinyl monomers having a high refractive index, siloxane functional vinyl compounds, polyethylene glycol-silicone co-monomers having vinyl groups, tris acrylate, pyrrole, liquid crystalline vinyl monomers, liquid crystalline vinyl polymers, and combinations thereof.

6. The kit of claim 1, wherein the initiator is selected from the group consisting of redox initiators, free radical initiators, radiation, and combinations thereof.

7. The kit of claim 6, wherein the radiation is selected from the group consisting of heat, visible light, ultraviolet light, gamma ray, and electron beam.

8. The kit of claim 1, wherein the device comprises an endoscope.

9. The kit of claim 1, wherein the device comprises a balloon catheter.

* * * * *